(12) United States Patent
Granada et al.

(10) Patent No.: US 7,396,538 B2
(45) Date of Patent: Jul. 8, 2008

(54) APPARATUS AND METHOD FOR DELIVERY OF MITOMYCIN THROUGH AN ELUTING BIOCOMPATIBLE IMPLANTABLE MEDICAL DEVICE

(75) Inventors: Juan F. Granada, Pearland, TX (US); Simon M. Furnish, New York, NY (US)

(73) Assignee: Endovascular Devices, Inc., Humble, TX (US)

( * ) Notice: Subject to any disclaimer, the term of this patent is extended or adjusted under 35 U.S.C. 154(b) by 573 days.

(21) Appl. No.: 10/672,679

(22) Filed: Sep. 26, 2003

(65) Prior Publication Data

US 2004/0098118 A1 May 20, 2004

Related U.S. Application Data

(60) Provisional application No. 60/413,833, filed on Sep. 26, 2002.

(51) Int. Cl.
*A61F 2/00* (2006.01)
(52) U.S. Cl. .................. 424/422; 623/1.42
(58) Field of Classification Search ....... 623/1.42–1.48; 424/422, 426; 428/36.9
See application file for complete search history.

(56) References Cited

U.S. PATENT DOCUMENTS

| | | | |
|---|---|---|---|
| 4,642,267 A | 2/1987 | Creasy et al. | 428/413 |
| 4,978,332 A | 12/1990 | Luck et al. | 604/19 |
| 5,069,899 A | 12/1991 | Whitbourne et al. | 424/56 |
| 5,153,252 A | 10/1992 | Skora | 524/372 |
| 5,216,011 A | 6/1993 | Paborji et al. | 514/410 |
| 5,286,254 A | 2/1994 | Shapland et al. | 604/21 |
| 5,342,348 A | 8/1994 | Kaplan | 604/891.1 |
| 5,355,832 A | 10/1994 | Loh et al. | 118/723 MW |
| 5,374,739 A | 12/1994 | Kaneko et al. | 548/422 |
| 5,447,799 A | 9/1995 | Loh et al. | 428/448 |
| 5,449,382 A | 9/1995 | Dayton | 623/1.15 |
| 5,464,650 A | 11/1995 | Berg et al. | 427/2.3 |

(Continued)

FOREIGN PATENT DOCUMENTS

WO  WO 03/064944  5/2003

(Continued)

OTHER PUBLICATIONS

International Search Report based on PCT/US03/30613 dated Jul. 9, 2004.

(Continued)

*Primary Examiner*—Suzette Gherbi
(74) *Attorney, Agent, or Firm*—Greenberg Traurig, LLP; David J. Dykeman

(57) ABSTRACT

The present invention is an apparatus and a method for delivery of mitomycin through an eluting biocompatible implantable medical device. A biocompatible drug release matrix comprises a biocompatible drug release matrix and a drug incorporated into the biocompatible drug release matrix. The drug has antibiotic and anti-proliferative properties and is an analogue related to the quinone-containing alkylating agents of a mitomycin family. The drug is initially released from the biocompatible drug release matrix at a faster rate followed by a release at a slower rate. The drug release rate maintains tissue level concentrations of the drug for at least two weeks after implantation of the medical device. The present invention provides a coating for a vascular prosthesis that elutes the drug at a controlled rate to inhibit proliferation of smooth muscle cells causing restenosis.

99 Claims, 28 Drawing Sheets

U.S. PATENT DOCUMENTS

| | | | | |
|---|---|---|---|---|
| 5,525,348 | A | 6/1996 | Whitbourne et al. | 424/423 |
| 5,534,287 | A | 7/1996 | Lukic | 427/2.25 |
| 5,545,208 | A | 8/1996 | Wolff et al. | 623/1.22 |
| 5,554,182 | A | 9/1996 | Dinh et al. | 600/36 |
| 5,569,198 | A | 10/1996 | Racchini | 604/103.01 |
| 5,571,166 | A | 11/1996 | Dinh et al. | 128/898 |
| 5,578,075 | A | 11/1996 | Dayton | 623/1.15 |
| 5,591,227 | A | 1/1997 | Dinh et al. | 623/1.22 |
| 5,599,352 | A | 2/1997 | Dinh et al. | 128/898 |
| 5,609,629 | A | 3/1997 | Fearnot et al. | 623/1.42 |
| 5,624,411 | A | 4/1997 | Tuch | 604/265 |
| 5,628,730 | A | 5/1997 | Shapland et al. | 604/21 |
| 5,629,008 | A | 5/1997 | Lee | 424/426 |
| 5,670,558 | A | 9/1997 | Onishi et al. | 523/112 |
| 5,679,400 | A | 10/1997 | Tuch | 427/2.14 |
| 5,690,670 | A | 11/1997 | Davidson | 606/198 |
| 5,697,967 | A | 12/1997 | Dinh et al. | 128/898 |
| 5,717,030 | A * | 2/1998 | Dunn et al. | 523/111 |
| 5,725,567 | A | 3/1998 | Wolff et al. | 623/1.42 |
| 5,731,087 | A | 3/1998 | Fan et al. | 428/412 |
| 5,776,184 | A | 7/1998 | Tuch | 623/1.11 |
| 5,788,979 | A | 8/1998 | Alt et al. | 424/426 |
| 5,800,392 | A | 9/1998 | Racchini | 604/103.01 |
| 5,824,048 | A | 10/1998 | Tuch | 128/898 |
| 5,824,049 | A | 10/1998 | Ragheb et al. | 623/1.44 |
| 5,837,008 | A | 11/1998 | Berg et al. | 128/898 |
| 5,837,313 | A | 11/1998 | Ding et al. | 427/2.21 |
| 5,843,172 | A | 12/1998 | Yan | 623/1.42 |
| 5,851,217 | A | 12/1998 | Wolff et al. | 606/191 |
| 5,851,231 | A | 12/1998 | Wolff et al. | 623/1.42 |
| 5,871,535 | A | 2/1999 | Wolff et al. | 128/898 |
| 5,879,697 | A | 3/1999 | Ding et al. | 424/422 |
| 5,980,972 | A | 11/1999 | Ding | 427/2.24 |
| 5,997,468 | A | 12/1999 | Wolff et al. | 600/36 |
| 5,997,517 | A | 12/1999 | Whitbourne | 604/265 |
| 6,004,346 | A | 12/1999 | Wolff et al. | 623/23.71 |
| 6,005,020 | A | 12/1999 | Loomis | 523/105 |
| 6,013,099 | A | 1/2000 | Dinh et al. | 623/1.15 |
| 6,042,875 | A | 3/2000 | Ding et al. | 427/2.24 |
| 6,096,070 | A | 8/2000 | Ragheb et al. | 623/1 |
| 6,106,454 | A | 8/2000 | Berg et al. | 600/3 |
| 6,110,483 | A | 8/2000 | Whitbourne et al. | 424/423 |
| 6,153,252 | A | 11/2000 | Hossainy et al. | 427/2.3 |
| 6,156,348 | A | 12/2000 | Santos et al. | 424/501 |
| 6,171,609 | B1 | 1/2001 | Kunz | 424/422 |
| 6,179,817 | B1 | 1/2001 | Zhong | 604/265 |
| 6,187,370 | B1 | 2/2001 | Dinh et al. | 427/2.24 |
| 6,197,051 | B1 | 3/2001 | Zhong | 623/1.46 |
| 6,197,320 | B1 | 3/2001 | Shalaby | 424/408 |
| 6,203,536 | B1 | 3/2001 | Berg et al. | 604/500 |
| 6,203,551 | B1 | 3/2001 | Wu | 606/108 |
| 6,273,908 | B1 | 8/2001 | Ndondo-Lay | 623/1.43 |
| 6,306,176 | B1 | 10/2001 | Whitbourne | 623/23.59 |
| 6,316,018 | B1 | 11/2001 | Ding et al. | 424/423 |
| 6,316,522 | B1 | 11/2001 | Loomis et al. | 523/105 |
| 6,344,035 | B1 | 2/2002 | Chudzik et al. | 604/265 |
| 6,346,110 | B2 | 2/2002 | Wu | 606/108 |
| 6,358,557 | B1 | 3/2002 | Wang et al. | 427/2.24 |
| 6,364,856 | B1 | 4/2002 | Ding et al. | 604/103.02 |
| 6,368,611 | B1 | 4/2002 | Whitbourne et al. | 424/411 |
| 6,387,379 | B1 | 5/2002 | Goldberg et al. | 424/400 |
| 6,569,195 | B2 | 5/2002 | Yang et al. | 623/1.46 |
| 6,399,144 | B2 | 6/2002 | Dinh et al. | 427/2.24 |
| 6,419,692 | B1 | 7/2002 | Yang et al. | 623/1.15 |
| 6,451,348 | B1 | 9/2002 | Jeong et al. | 424/486 |
| 6,471,980 | B2 | 10/2002 | Sirhan et al. | 424/423 |
| 6,482,444 | B1 | 11/2002 | Bellantone et al. | 424/618 |
| 6,494,862 | B1 | 12/2002 | Ray et al. | 604/96.01 |
| 6,503,556 | B2 | 1/2003 | Harish et al. | 427/2.24 |
| 6,503,954 | B1 | 1/2003 | Bhat et al. | 514/772.2 |
| 6,506,437 | B1 | 1/2003 | Harish et al. | 427/2.25 |
| 6,534,693 | B2 | 3/2003 | Fischell et al. | 602/43 |
| 6,540,776 | B2 | 4/2003 | Sanders Millare et al. | 623/1.15 |
| 6,544,582 | B1 | 4/2003 | Yoe | 427/2.24 |
| 6,545,097 | B2 | 4/2003 | Pinchuk et al. | 525/240 |
| 6,730,313 | B2 * | 5/2004 | Helmus et al. | 424/423 |
| 6,733,767 | B2 * | 5/2004 | Chern et al. | 424/426 |
| 7,160,592 | B2 * | 1/2007 | Rypacek et al. | 428/36.9 |
| 2001/0001824 | A1 | 5/2001 | Wu | 606/108 |
| 2001/0014717 | A1 | 8/2001 | Hossainy et al. | 525/60 |
| 2001/0018469 | A1 | 8/2001 | Chen et al. | 523/121 |
| 2001/0018919 | A1 | 9/2001 | Kutzko et al. | 128/898 |
| 2001/0044651 | A1 | 11/2001 | Steinke et al. | 623/1.16 |
| 2001/0049349 | A1 | 12/2001 | Chinery et al. | 514/1 |
| 2002/0018795 | A1 * | 2/2002 | Whitbourne et al. | 424/414 |
| 2002/0052404 | A1 * | 5/2002 | Hunter et al. | 514/449 |
| 2002/0055666 | A1 | 5/2002 | Hunter et al. | 600/1 |
| 2002/0082682 | A1 | 6/2002 | Barclay et al. | 623/1.22 |
| 2002/0123505 | A1 | 9/2002 | Mollison et al. | 514/291 |
| 2002/0123788 | A1 | 9/2002 | Millare et al. | 623/1.13 |
| 2002/0123801 | A1 | 9/2002 | Pacetti et al. | 623/1.46 |
| 2002/0133224 | A1 | 9/2002 | Bajgar et al. | 623/1.39 |
| 2002/0155092 | A1 | 10/2002 | Leong et al. | 424/78.37 |
| 2002/0165423 | A1 | 11/2002 | Forman | 600/3 |
| 2002/0183763 | A1 | 12/2002 | Callol et al. | 606/108 |
| 2002/0193475 | A1 | 12/2002 | Hossainy et al. | 524/113 |
| 2003/0004564 | A1 | 1/2003 | Elkins et al. | 623/1.15 |
| 2003/0017190 | A1 | 1/2003 | Sirhan et al. | 424/426 |
| 2003/0027863 | A1 | 2/2003 | Cruz et al. | 514/546 |
| 2003/0040712 | A1 | 2/2003 | Ray et al. | 604/173 |
| 2003/0040790 | A1 | 2/2003 | Furst et al. | 623/1.11 |
| 2003/0054090 | A1 | 3/2003 | Hansen | 427/2.1 |
| 2003/0065382 | A1 | 4/2003 | Fischell et al. | 623/1.15 |

OTHER PUBLICATIONS

Strauss et al., "Late Effects of Locally Delivered Mitomycin C on Formation of Neointima and on Vasomotor Response to Acetylcholine", Jul. 1994, *Coronary Artery Disease*, vol. 5 No. 7, p. 633-641.

* cited by examiner

Table: Total Dose Estimate In A 13 mm Stent For Loss Factors From 1% to 100%

| Loss Factor | Total Dose | | |
|---|---|---|---|
| | per 13 mm stent (µg) | per mm stent length (µg/mm) | per stent surface area (µg/mm²) |
| 100% | 13.2 | 1.0 | 0.17 |
| 75% | 17.6 | 1.4 | 0.22 |
| 50% | 26.4 | 2.0 | 0.33 |
| 25% | 52.8 | 4.1 | 0.66 |
| 10% | 132.0 | 10.2 | 1.65 |
| 5% | 264.0 | 20.3 | 3.30 |
| 1% | 1320.0 | 101.5 | 16.50 |

FIG. 32

APPARATUS AND METHOD FOR DELIVERY OF MITOMYCIN THROUGH AN ELUTING BIOCOMPATIBLE IMPLANTABLE MEDICAL DEVICE

RELATED APPLICATIONS

This application claims the benefit of U.S. Provisional Application Ser. No. 60/413,833, filed Sep. 26, 2002, the entirety of which is hereby incorporated herein by reference.

FIELD OF THE INVENTION

The present invention relates to a medical device, and more particularly to an apparatus and a method for delivery of mitomycin through an eluting biocompatible implantable medical device.

BACKGROUND OF THE INVENTION

Coronary artery disease (CAD) is the leading cause of death in the western world. In the United States, more than 13 million people are diagnosed with CAD every year. Since its introduction in the late 1970's, Percutaneous Transluminal Coronary Angioplasty (PTCA), also known as balloon angioplasty, emerged as the principal, less invasive alternative to Coronary Artery Bypass Grafting (CABG). A limitation of PTCA is a high rate of restenosis, a condition in which the vasculature renarrows within six months of a revascularization treatment to less than 50% of its original size. Restenosis is caused by the activation and growth of vascular smooth muscle cells that make the vessel more susceptible to complete blockage. Studies have shown restenosis affects between about 25% to about 45% of PTCA patients within six months after the procedure.

Coronary stents lower restenosis rates by decreasing the vascular recoil after balloon angioplasty. A stent is a mesh-like tubular device resembling a spring that is capable of propping open a clogged artery when placed within the vessel using a specialized delivery device such as the balloon catheter used in angioplasty procedures. The stent serves as a permanent scaffolding for the newly widened vessel. Stents are percutaneous non-surgical treatments that lower the restenosis rate of PTCA by achieving a larger final luminal area. To date, stents have reduced the likelihood of acute closure after coronary revascularization procedures.

Immediately after the implantation of a stent, the healing process within the vasculature causes an overgrowth of cells and substances within and around the stent, increasing the potential for a recurrence of the blockage. The healing process leads to neointima formation which is initiated by activation of vascular smooth muscle cells, followed by emigration and proliferation with subsequent elaboration of the abundant extracellular matrix by the smooth muscle cells. As the smooth muscle cells grow on and around the stent, the vasculature renarrows and restenosis continues. Inhibition of smooth muscle cell proliferation appears to prevent the development of subsequent blockages within the vasculature as the diameter of the passageway through the vasculature is reduced by the smooth muscle cell proliferation.

Several therapeutic agents have been used in combination with stents to inhibit restenosis in the prior art. U.S. Pat. No. 6,569,195 to Yang et al. discloses a stent having a polymeric coating for controllably releasing an included active agent. The Yang et al. coating includes a blend of a first co-polymer having a first, high release rate and a second co-polymer having a second, lower release rate relative to the first release rate. U.S. Pat. No. 6,171,609 to Kunz discloses a therapeutic inhibitor of vascular smooth muscle cells. The Kunz device utilizes a cytoskeletal inhibitor and an amount of a cytostatic therapeutic agent to inhibit stenosis or reduce restenosis.

U.S. Pat. No. 6,344,035 to Chudzik et al. discloses a coating composition for use with medical devices to improve the ability of the device to release a bioactive agent in vivo. The coating composition includes the bioactive agent with a mixture of a first polymer component such as poly(butyl methacrylate) and a second polymer component such as poly(ethylene-co-vinyl acetate). The Chudzik et al. device requires the mixture of a first polymer component such as poly(butyl methacrylate) and a second polymer component such as poly(ethylene-co-vinyl acetate). In addition, the Chudzik et al. device is limited by the ability of titrating the release rate of the bioactive agent.

U.S. Pat. No. 5,788,979 to Alt et al. discloses a biodegradable coating with inhibitory properties for application to biocompatible materials. The Alt et al. device comprises a coating material comprising an anticoagulant drug wherein the coating material is adhesively applied to a surface of the biocompatible material in a substantially continuous overlying layer having a formulation, pattern and thickness selected according to a period of time in which the coating material exhibits the inhibitory action. The Alt et al. coating has shown a potential of triggering a severe vessel inflammation by activating cells after the polymer of the biodegradable coating is broken down in the vessel.

The prior art is ineffective at inhibiting restenosis and subjects patients to undesirable health risks. The prior art is limited to mixtures of specific polymer components and does not provide adequate control of the drug elution to treat a lesion. In addition, the prior art has shown a potential of triggering a severe vessel inflammation by activating cells after the polymer is broken down in the vessel. Therefore, there remains a need in the art for a method of treating a localized area of a diseased vessel after delivery of a biocompatible implantable medical device that can control the elution of the drug and is does not harm the patient.

SUMMARY OF THE INVENTION

A biocompatible drug release matrix for a medical device comprises a biocompatible polymer matrix and a drug incorporated into the biocompatible polymer matrix, wherein the biocompatible polymer matrix is co-solubilized with the drug in a solvent to form a solution and the solvent is evaporated from the solution.

A biocompatible implantable medical device for delivering a drug to a treatment area in a vasculature of a body comprises: a tubular body having a proximal end, a distal end and a longitudinal axis therebetween; a proximal end band at the proximal end of the tubular body, a distal end band at the distal end of the tubular body and a plurality of intermediate bands between the proximal end band and the distal end band; a plurality of circumferential rows of links engaging the proximal end band, the plurality of intermediate bands and the distal end band to form the tubular body; and an elution layer comprising a biocompatible drug release matrix applied to the surface of the biocompatible implantable medical device having a biocompatible polymer matrix solubilized with the drug in a solvent to form a solution and the solvent is evaporated, wherein the drug is released from the biocompatible drug release matrix after implantation of the biocompatible implantable medical device to prevent restenosis.

A method of inhibiting the growth of smooth muscle cells to inhibit restenosis comprising: providing a biocompatible implantable medical device; preparing a biocompatible polymer matrix; co-solubilizing the biocompatible polymer matrix with a drug in a solvent to form a biocompatible drug release matrix; applying the biocompatible drug release matrix to the biocompatible implantable medical device to form an elution layer of the biocompatible drug release matrix on the biocompatible implantable medical device; allowing the solvent to evaporate; and implanting the biocompatible implantable medical device into a vasculature of a body.

A method of inhibiting the proliferation of smooth muscle cells after a stent implantation comprising: providing a stent; preparing a biocompatible polymer matrix; co-solubilizing the biocompatible polymer matrix with a drug in a solvent to form a solution; applying the solution onto the stent to form an elution layer of a biocompatible drug release matrix on the biocompatible implantable medical device; allowing the solvent to evaporate; engaging the stent onto a balloon of a balloon catheter; delivering the balloon catheter with the stent engaged onto the balloon of the balloon catheter into a vasculature of a body to a treatment site; and inflating the balloon of the balloon catheter to increase a diameter of the stent to implant the stent.

A biocompatible drug release matrix for a medical device comprises a biocompatible drug eluting matrix and a drug incorporated into the biocompatible drug eluting matrix, wherein the drug is an analogue related to the quinone-containing alkylating agents of a mitomycin family.

A method of inhibiting restenosis comprising: providing a medical device; applying a biocompatible drug eluting matrix comprising a biocompatible polymer matrix incorporating an analogue related to the quinone-containing alkylating agents of a mitomycin family to the medical device; and implanting the biocompatible implantable medical device into a vessel to elute the analogue related to the quinone-containing alkylating agents of a mitomycin family.

The drug has antibiotic properties and anti-proliferative properties. The drug is an analogue related to the quinone-containing alkylating agents of a mitomycin family. The preferred drug is mitomycin C. The biocompatible drug release matrix releases the drug at a rate sufficient to maintain tissue level concentrations of the drug from about 0.01 micrograms per milliliter to about 25 micrograms per milliliter of the surrounding tissue for at least two weeks after implantation of the medical device. The biocompatible drug release matrix may be incorporated within a vascular prosthesis, be applied as a coating to a surface of the vascular prosthesis or comprise a film which covers the vascular prosthesis.

The present invention is an apparatus and a method for delivery of mitomycin through an eluting biocompatible implantable medical device. Mitomycin C causes inhibition of smooth muscle cell proliferation in an anaerobic (low oxygen) environment. The present invention provides an effective method of treating a localized area of a diseased vasculature after delivery of a biocompatible implantable medical device that provides a coating that elutes mitomycin C at a controlled rate that inhibits the proliferation of smooth muscle cells causing restenosis, is reliable in consistently treating the localized area over a period of time and does not adversely affect healthy tissue proximal to an area of treatment.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 32 is a table showing a total dose estimate of mitomycin C in a 13 mm stent for loss factors from 1% to 100%.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

Figure 1:
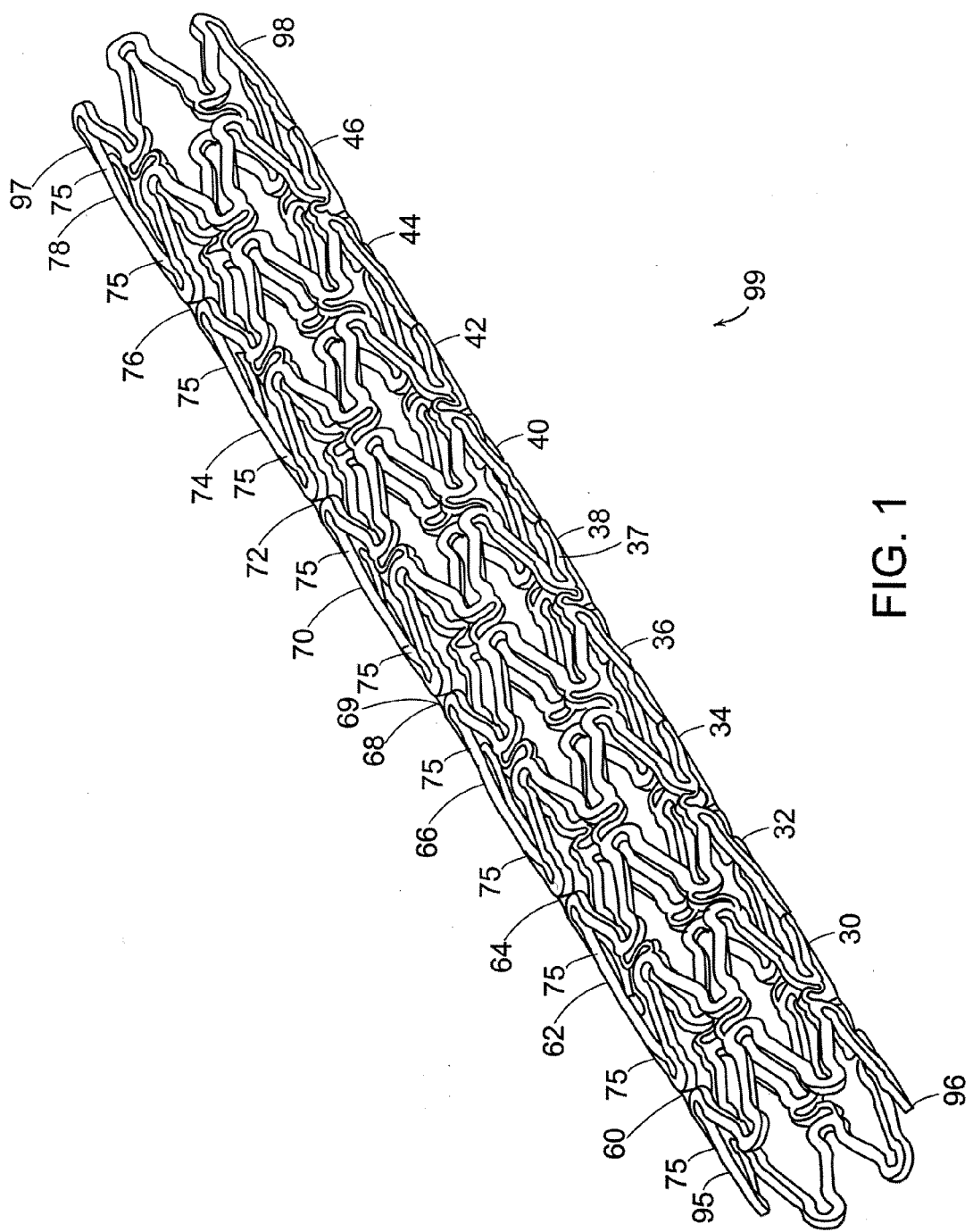
FIG. 1 is a perspective view of a biocompatible implantable medical device of the present invention capable of inhibiting restenosis.

An apparatus for a biocompatible implantable medical device comprising a biocompatible drug release matrix is illustrated generally at 99 in FIG. 1. In a preferred embodiment of the present invention, the biocompatible implantable medical device 99 is a stent. The present invention can be used with stents known in the art including, but not limited to, the stents described in Assignee's co-pending patent applications Ser. No. 09/624,812 and Ser. No. 10/410,950, the entirety of these applications are hereby incorporated herein by reference. In another embodiment of the present invention, the biocompatible implantable medical device 99 is a catheter, a vascular prosthesis, an intravenous canule or a similar device. The biocompatible implantable medical device 99 has a tubular body comprising a plurality of circumferential bands 37 and a plurality of circumferential row of links 69 that engage the plurality of circumferential bands 37. A circumferential row of links engages adjacent circumferential bands. The biocompatible implantable medical device 99 comprises a proximal end band 98 located at a proximal end 97, a distal end band 96 located at a distal end 95 and at least one intermediate band located between proximal end band 98 and distal end band 96. In the embodiment of the present invention shown in FIG. 1, the biocompatible implantable medical device 99 comprises the proximal end band 98, the distal end band 96 and intermediate circumferential bands 30, 32, 34, 36, 38, 40, 42, 44 and 46. The number of the circumferential bands 37, the number of the circumferential rows of links 69, a length of the biocompatible implantable medical device 99 and a diameter of the biocompatible implantable medical device 99 vary depending upon the application of the biocompatible implantable medical device 99. The plurality of circumferential bands 37 are arranged axially end to end, extending from the proximal end 97 of the biocompatible implantable medical device 99 to the distal end 95 of the biocompatible implantable medical device 99. Each of the plurality of the circumferential bands 37 is comprised of a continuous strand 75 that is shaped in a zig-zag pattern shown in FIG. 1. The plurality of circumferential row of links 69 engage adjacent circumferential bands. In the embodiment of the present invention shown in FIG. 1, circumferential rows of links 60, 62, 64, 66, 68, 70, 72, 74, 76 and 78 engage adjacent circumferential bands. For example, the circumferential row of links 64 engages intermediate circumferential bands 32 and 34.

Figure 2:
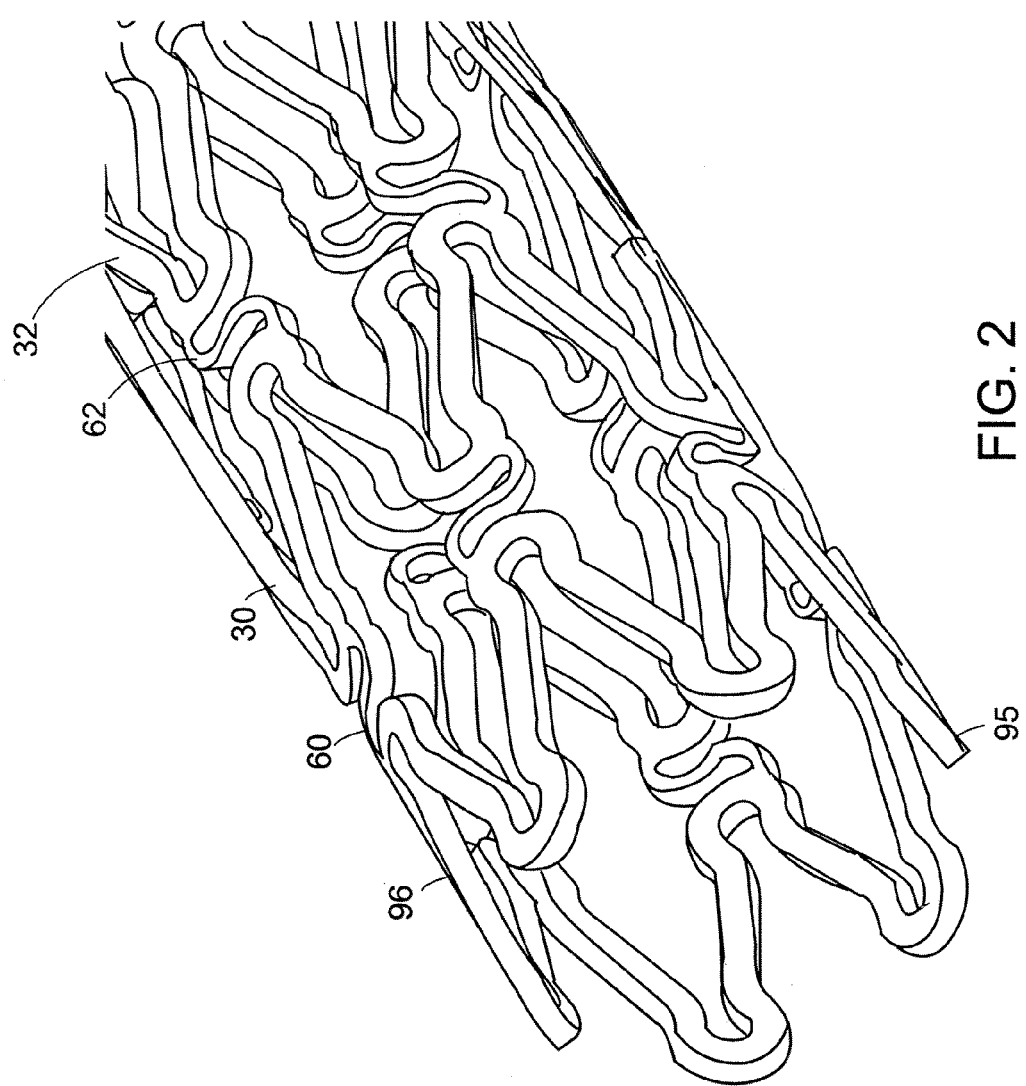
FIG. 2 is an enlarged fragmentary perspective view of a distal end of the biocompatible implantable medical device of the present invention.

FIG. 2 shows an enlarged fragmentary view of the distal end 95 of the biocompatible implantable medical device 99 of the present invention. FIG. 2 illustrates the tubular shape of the biocompatible implantable medical device 99. FIG. 2 shows the circumferential row of links 60 engaging the distal end band 96 and the intermediate band 30. In addition, circumferential row of link 62 engages the adjacent intermediate bands 30 and 32.

Figure 3:
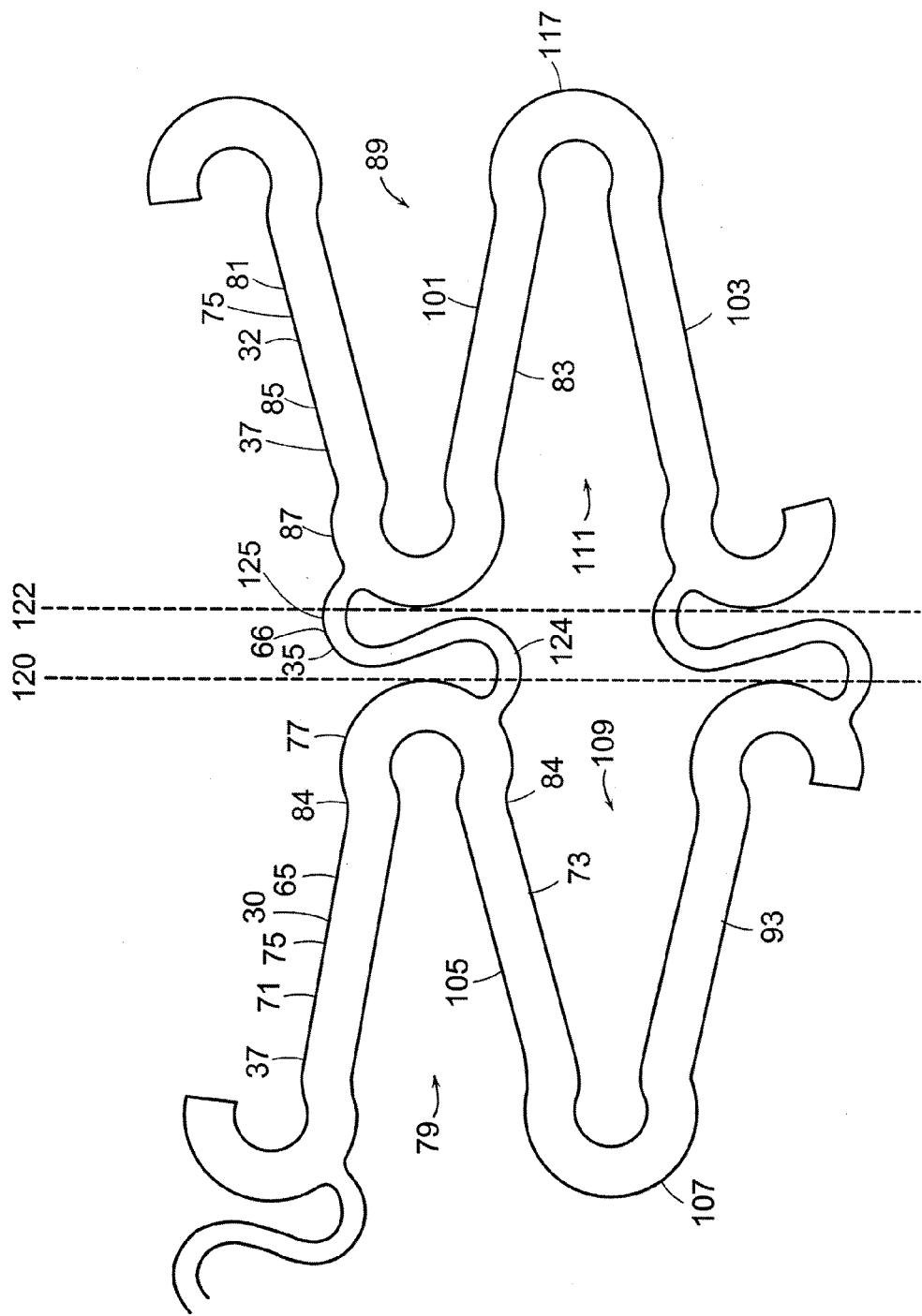
FIG. 3 is an enlarged view of a biocompatible implantable medical device of the present invention showing adjacent circumferential bands engaged by a plurality of links.

FIG. 3 shows a portion of adjacent circumferential bands 30, 32 and a link 35 from circumferential row of link 62 where the link 35 engages the intermediate band 30 to the intermediate band 32. A portion of the strand 75 for intermediate circumferential band 30 comprises a loop 65 that further comprises two legs 71 and 73. The legs 71 and 73 converge to form a bend 77 and a gap 79 opposing the bend 77. In a continuing pattern, a loop 105 is formed by the leg 73 and a leg 93 to form a bend 107 with a gap 109 opposing the bend 107. In a similar manner, a portion of the strand 75 for adjacent circumferential band 36 comprises a loop 85 that further comprises a leg 81 and a leg 83. The leg 81 and the leg 83 converge to form a bend 87 with a gap 89 opposing the bend 87. In a continuing pattern for circumferential band 32, a loop 101 comprises the leg 83 and the leg 103, with the leg 83 and the leg 103 converging to form a bend 117 with a gap 111 opposing the bend 117. Each strand 75 for each circumferential band 37 comprises a plurality of loops with each circumferentially adjacent loop sharing a common leg.

As shown in FIG. 3, the circumferential bands 30 and 32 are circumferentially formed of alternating bends and gaps. For example, an edge 120 of the circumferential band 30, (shown as a broken line in FIG. 3) is formed partially of the bend 77 and the gap 109. Similarly, an edge 122 of the circumferential band 32, (shown as a broken line in FIG. 3) is formed partially of the bend 87 and the gap 111. Within each of the plurality of the circumferential bands 37, a bend is longitudinally opposed by a gap. For example, with respect to the circumferential band 30, the bend 77 longitudinally opposes the gap 79 and the bend 107 longitudinally opposes the gap 109. Adjacent circumferential bands are longitudinally positioned so the bends forming the edge of one circumferential band are aligned with the bends forming the opposing edge of the adjacent circumferential band. For example, the bend 77 of the circumferential band 30 is adjacent to the bend 87 of the circumferential band 32.

The plurality of the circumferential rows of links 69 engage the plurality of circumferential bands 37. In a preferred embodiment of the present invention, each individual link from the plurality of circumferential rows of links 69 is formed by two oppositely oriented curves that are engaged to form a link. In a preferred embodiment of the present invention, the two oppositely oriented curves form a S link. In another embodiment of the present invention, the two oppositely oriented curves form a curved link. As shown in FIG. 3, the link 35 that engages the bend 77 of the circumferential band 30 to the bend 87 of the circumferential band 32 comprises a lower curve 124 and an upper curve 125. When viewing the link 35 from the bend 77, a lower curve 124 extends in a downward direction and an upper curve 125 extends in an upward direction. Those skilled in the art will recognize that the two oppositely oriented curves can form a link of many shapes and be within the spirit and scope of the present invention.

In a preferred embodiment of the present invention shown in FIG. 3, the bends 77, 87, 107 and 117 are all radiused to greater than approximately 180 degrees. In another embodiment of the present invention, the bends 77, 87, 107 and 117 are all radiused to less than approximately 180 degrees. The bends 77, 87, 107 and 117 take the shape of a partial circle and engage the legs of the loops. For example, the bend 77 engages the leg 71 and the leg 73 of the loop 65. Narrowed portions are created between each of the bends and at the adjacent legs. For example, a narrowed portion 84 is formed between the bend 77 and the adjacent legs 71 and 73 respectively. Those skilled in the art will recognize that the bends can be radiused to any degree known in the art and be within the spirit and scope of the present invention.

Figure 4:
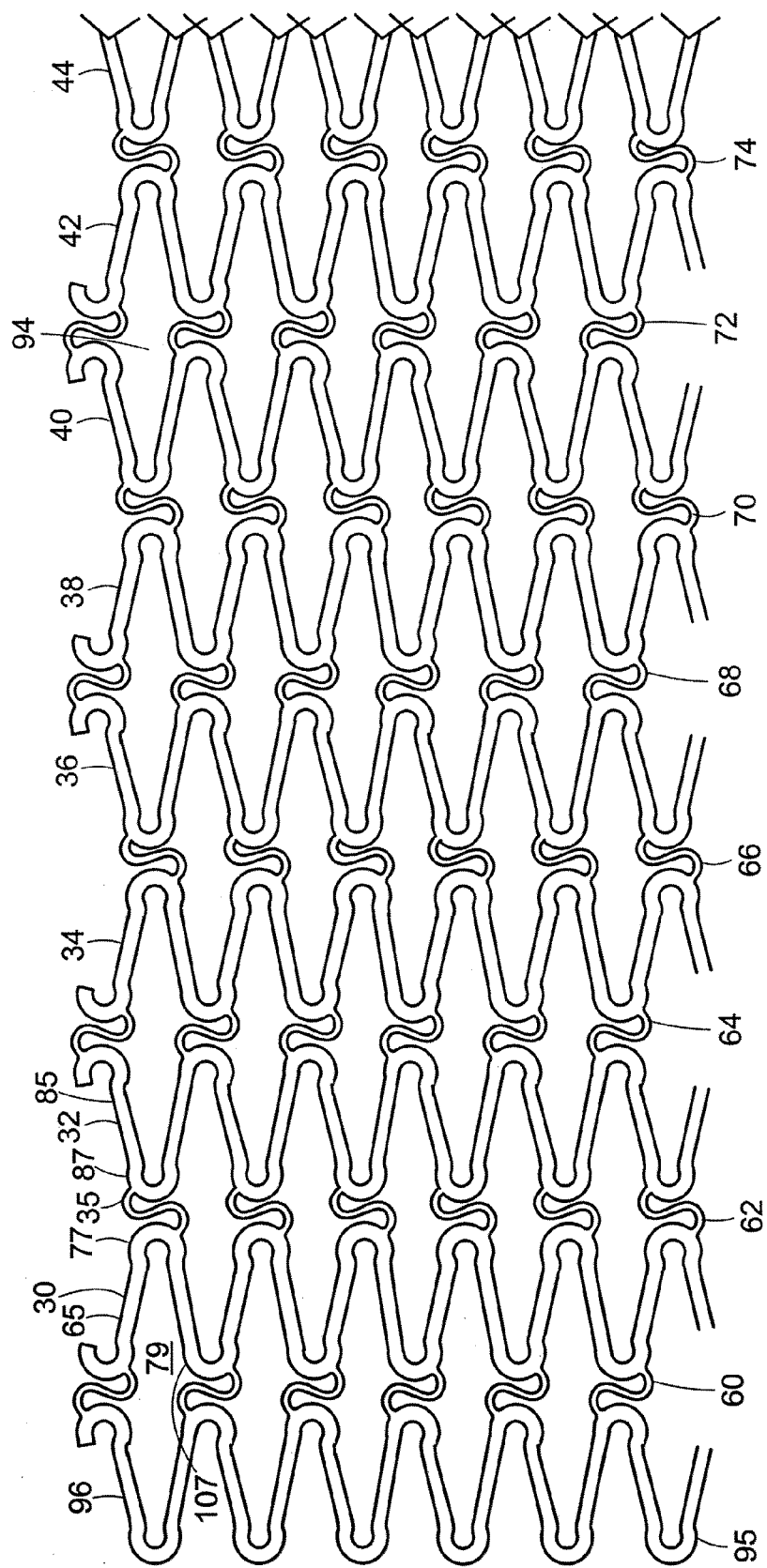
FIG. 4 is a flattened view of a portion of a biocompatible implantable medical device of the present invention.

FIG. 4 shows a flattened view of the tubular body of the biocompatible implantable medical device 99 of the present invention. The distal end bend 96 and the circumferential intermediate bands 30, 32, 34, 36, 38, 40 and 42 are constructed in a repeating pattern. The bends of each of the circumferential bands 96, 30, 32, 34, 36, 38, 40 and 42 extend alternately toward the distal end 95 of the biocompatible implantable medical device 99 and then toward the proximal end 97 of the biocompatible implantable medical device 99. In a preferred embodiment of the present invention, a link engages each pair of axially aligned opposing bends from the adjacent circumferential bands. More specifically, the bend 77 in the circumferential band 30 extends toward the proximal end 97 of the biocompatible implantable medical device 99 while the adjacent bend 87 of the circumferential band 32 extends toward the distal end 95 of the biocompatible implantable medical device 99. The construction of the biocompatible implantable medical device 99 allows for a plurality of closed cells 94. For each pair of axially aligned opposing bends, a link engages the axially aligned opposing bends, creating the closed cell configuration. Conversely, a configuration where each pair of axially aligned opposing bends does not comprise a link engaging the axially aligned opposing bends would create an open cell configuration.

Figure 5:
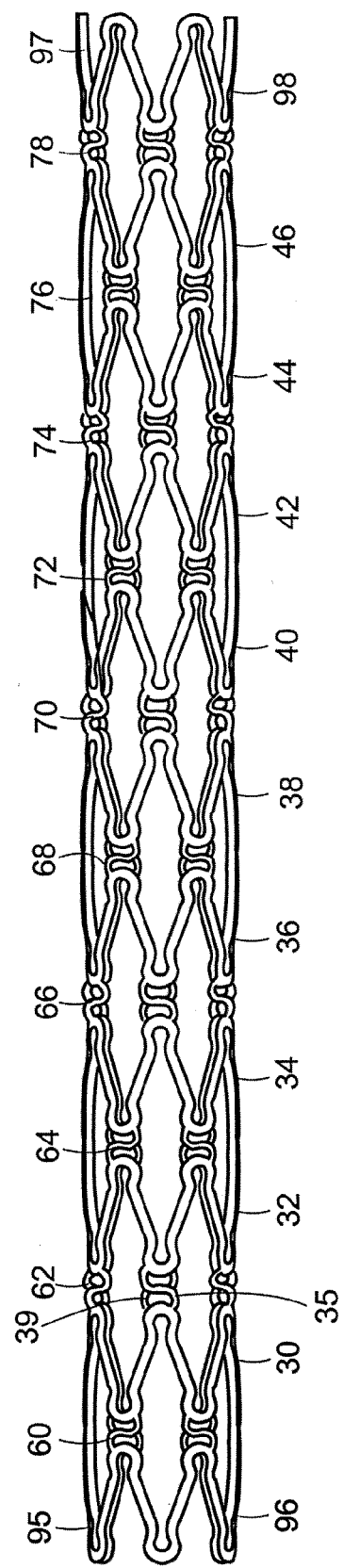
FIG. 5 is a side plan view of a biocompatible implantable medical device of the present invention.
Figure 6:
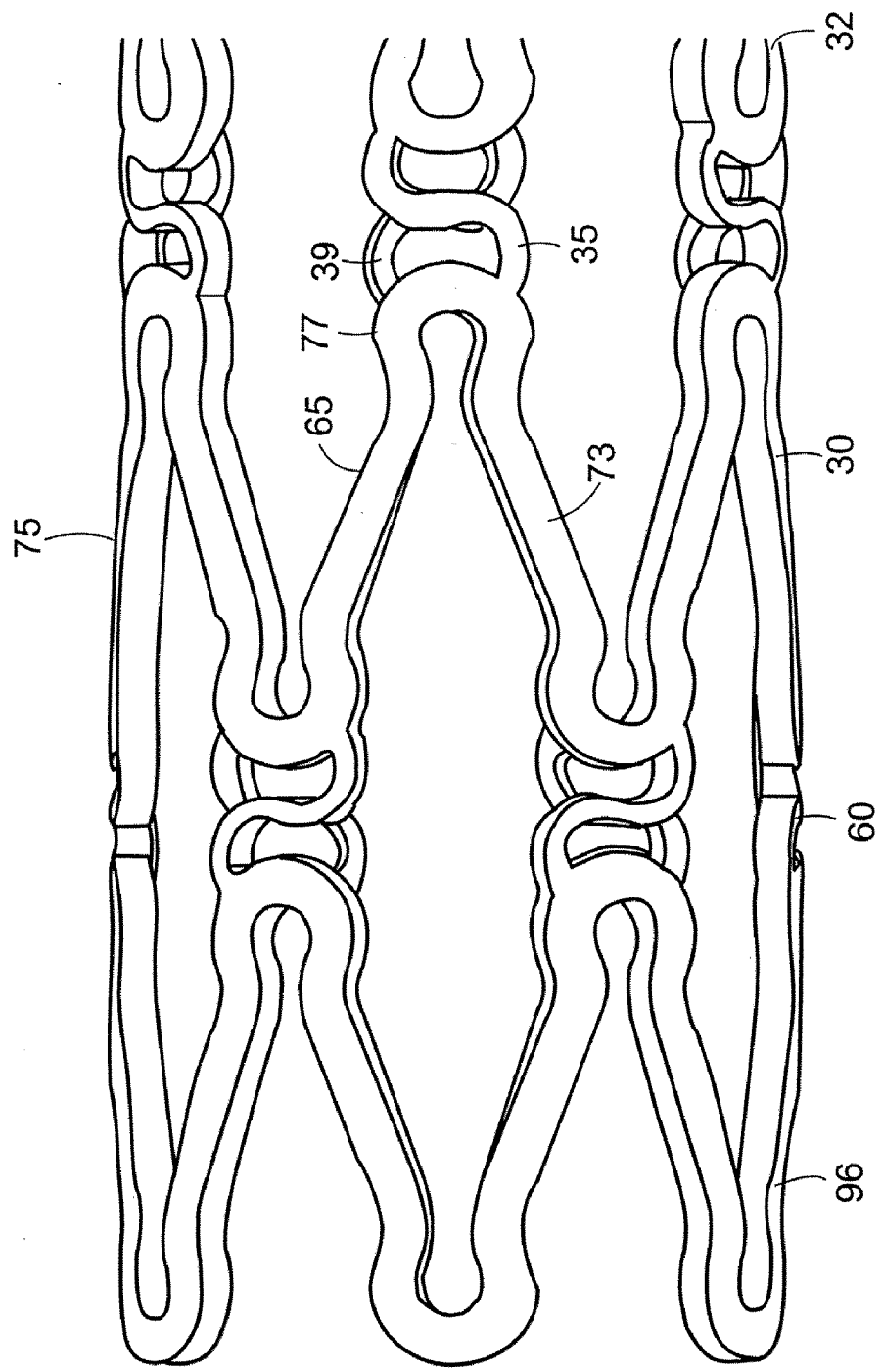
FIG. 6 is an enlarged side view of a distal end of the biocompatible implantable medical device of the present invention with a plurality of circumferential bands and a plurality of circumferential links.

FIG. 5 shows a side plan view of the biocompatible implantable medical device 99 of the present invention. FIG. 6 shows an enlarged side view of the distal end 95 of the biocompatible implantable medical device 99 of the present invention. FIG. 6 illustrates the tubular shape of the biocompatible implantable medical device 99 of the present invention. The loop 65 of intermediate circumferential band 30 is engaged to the adjacent loop of circumferential band 32 by the link 35. The link 39 is located behind the link 35, located approximately 180 degrees from the link 35.

Figure 7:
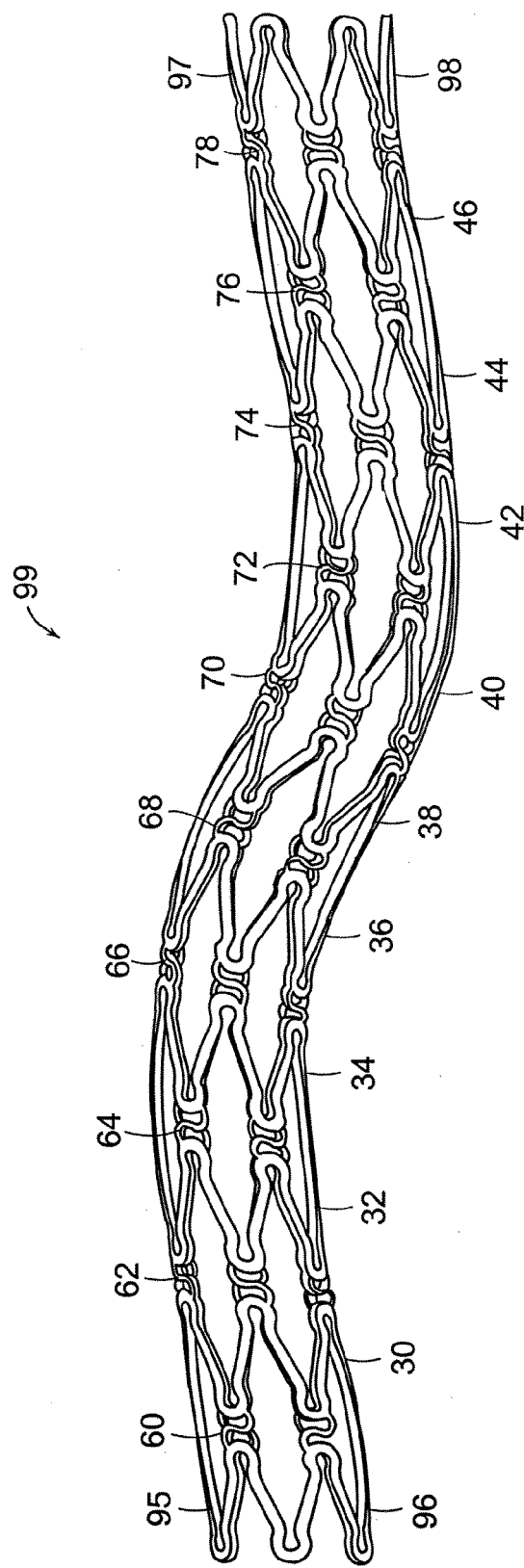
FIG. 7 is a side plan view of a biocompatible implantable medical device of the present invention in a flexed configuration.

FIG. 7 shows a side plan view of the biocompatible implantable medical device 99 of the present invention in a flexed configuration. In preferred embodiment of the present invention, the plurality of circumferential bands 37 and the plurality of circumferential row of links 69 are comprised of a pliable, shape sustaining material that allows the biocompatible implantable medical device 99 to be bent, deflected or flexed. The biocompatible implantable medical device 99 comprises a perforated tubular material in a design that optimizes the radial strength and the ability of the biocompatible implantable medical device 99 to be flexed, bent and deflected. The flexibility of the biocompatible implantable medical device 99 provides conformability in a vasculature of a body while still providing a relatively rigid distal end 95 and proximal end 97. The flexibility of the biocompatible implantable medical device 99 allows the biocompatible implantable medical device 99 to be inserted through the tortuous paths of the vasculature. The combination of bends radiused greater than approximately 180 degrees, multiple jointed loops of the plurality of circumferential bands 37 and the plurality of the circumferential row of links provides a range of expandability for the biocompatible implantable medical device 99. In addition, the jointed pattern of the biocompatible implantable medical device 99 provides conformability so that when the biocompatible implantable medical device 99 is deployed, the biocompatible implantable medical device 99 will conform to irregular contours of the walls of the vasculature.

Figure 8:
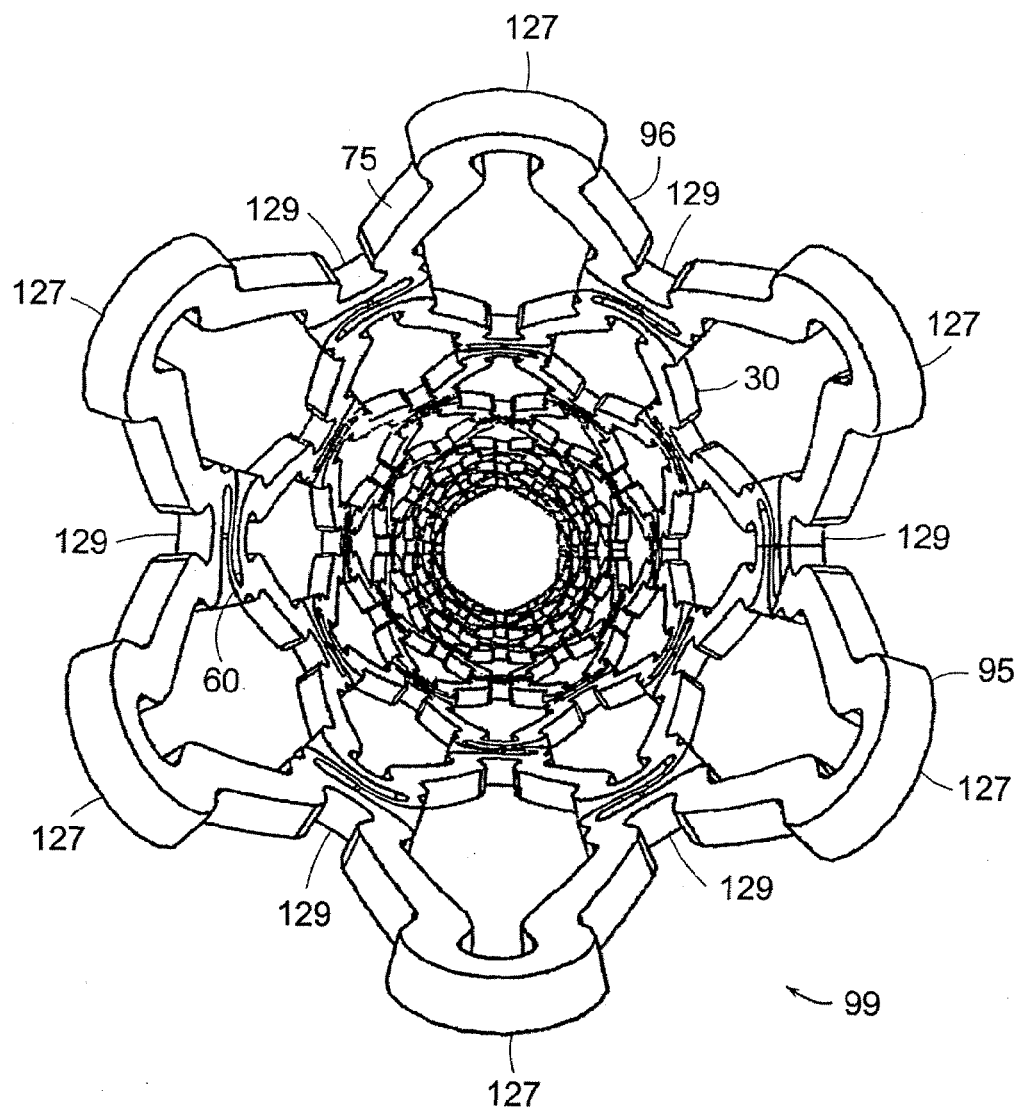
FIG. 8 is a front perspective view of a biocompatible implantable medical device of the present invention taken from a distal end of the biocompatible implantable medical device.
Figure 9:
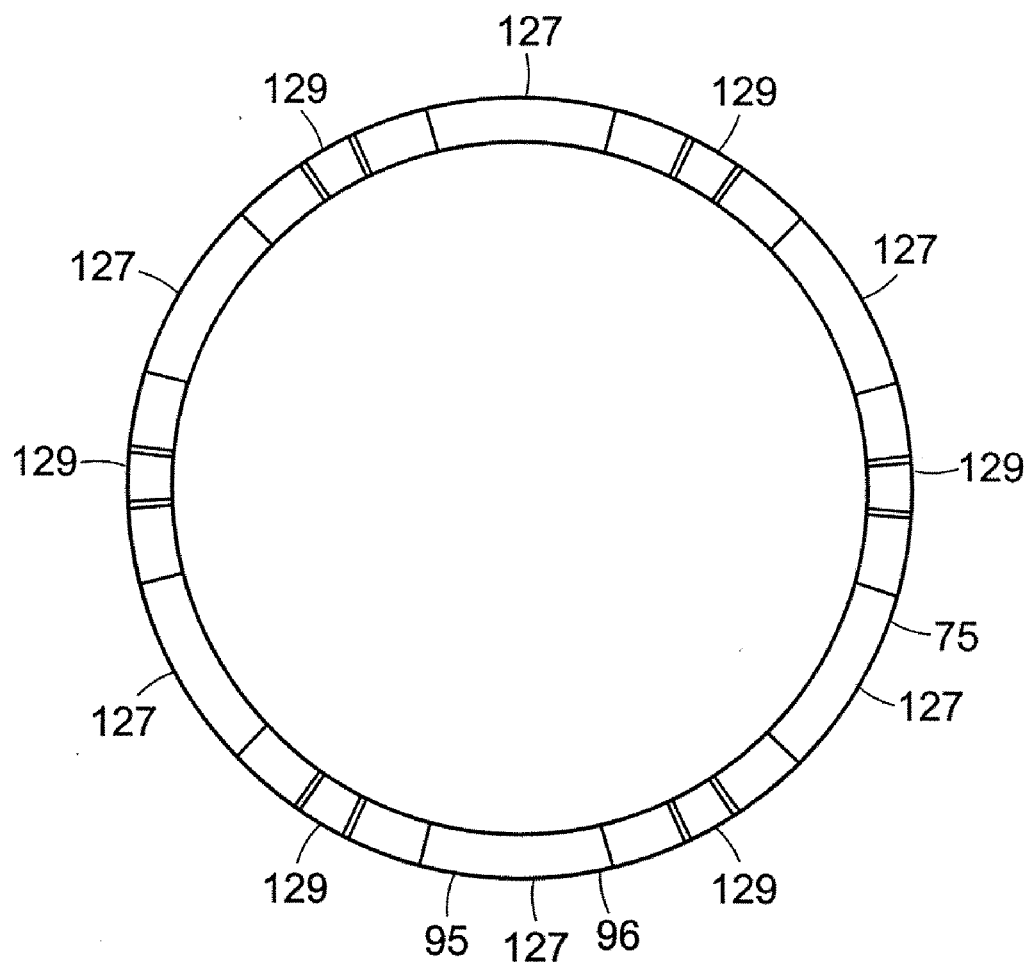
FIG. 9 is a front view of a biocompatible implantable medical device of the present invention taken from a distal end of the biocompatible implantable medical device.

FIG. 8 shows a front perspective view of the biocompatible implantable medical device 99 of the present invention taken from the distal end 95 of the biocompatible implantable medical device 99. FIG. 9 shows a front view of the biocompatible implantable medical device 99 of the present invention from the distal end 95 of the biocompatible implantable medical device 99. In the embodiment of the present invention shown in FIG. 8 and FIG. 9, the distal end band 96 comprises twelve loops and twelve bends with a total of six bends 127 located at the distal end 95 of the distal end band 96 and a total of six bends 129 located proximal to the six bends at the distal end 95 of distal end band 96. Those skilled in the art will recognize the circumferential bands can comprise any number of loops and bends and be within the spirit and scope of the present invention.

The effectiveness of the biocompatible implantable medical device 99 to inhibit the growth of smooth muscle cells is governed by providing an effective concentration of a drug throughout a treatment area over a necessary period of time to inhibit restenosis. The present invention includes several designs for the biocompatible implantable medical device 99 and several methods for incorporating the drug within the biocompatible implantable medical device 99. Transport of the drug to the treatment area can occur by direct exposure, diffusion, molecular bond degradation or other methods known in the art.

Figure 10:
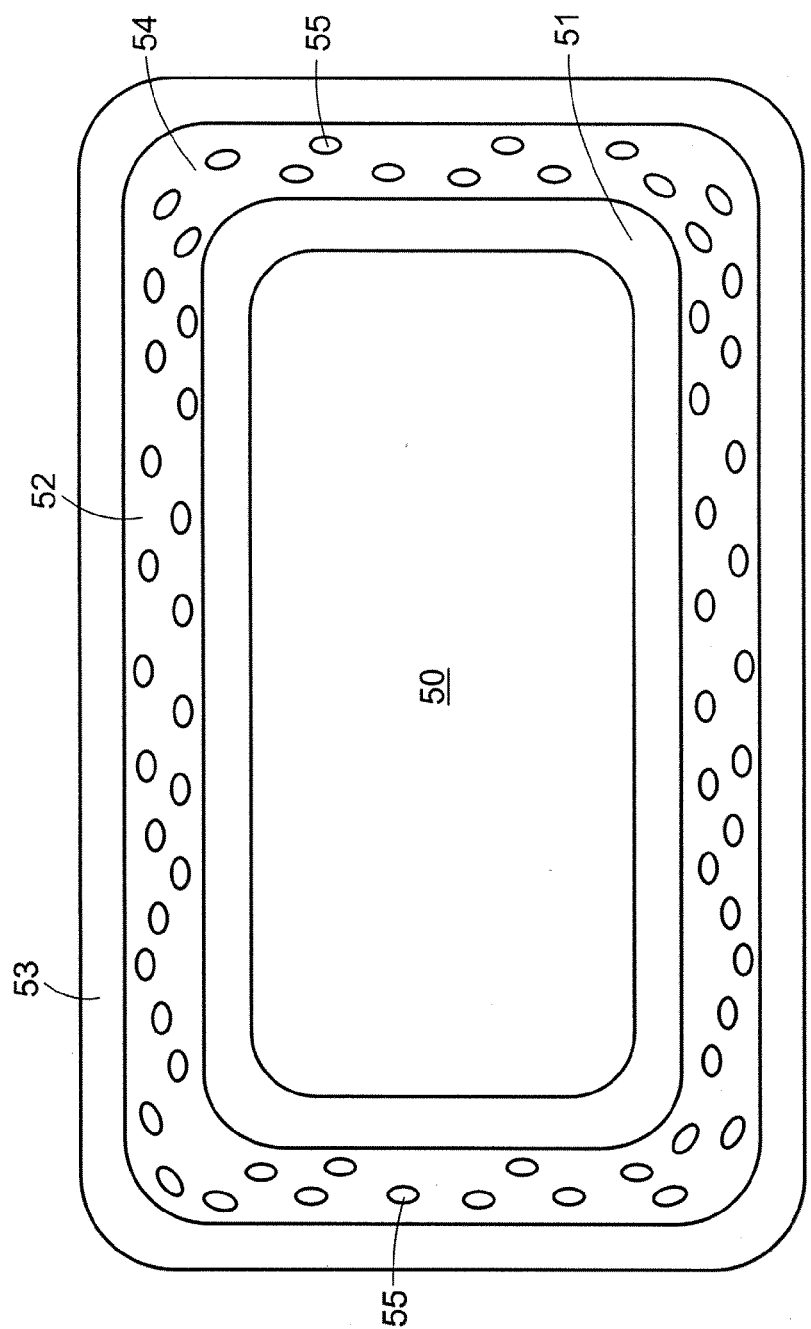
FIG. 10 is a cross section view of a strand of a biocompatible implantable medical device of the present invention with a strut surrounded by a first coating layer, a second coating layer and a third coating layer.

FIG. 10 shows a cross section view of an embodiment of a strand 75 of the biocompatible implantable medical device 99 of the present invention comprising a strut 50 surrounded by a primer layer 51, an elution layer 52 and a burst control layer 53. The primer layer 51 comprises a biocompatible polymer matrix 54 that improves the adhesion of the elution layer 52 to the strut 50. The elution layer 52 comprises a biocompatible polymer matrix 54 and a drug 55 that elutes to treat a tissue.

The burst control layer 53 controls and limits the kinetics of the burst dose of the drug 55 from the elution layer 52.

In a preferred embodiment of the present invention, the primer layer 51 comprises a biocompatible polymer matrix 54 with or without a drug. In another embodiment of the present invention, the primer layer 51 comprises the biocompatible polymer matrix 54 and a drug (not shown) incorporated into the biocompatible polymer matrix 54. In a preferred embodiment of the present invention, the elution layer 52 comprises a biocompatible drug release matrix having the biocompatible polymer matrix 54 and the drug 55 incorporated into the biocompatible polymer matrix 54. In the embodiment of the present invention shown in FIG. 10, the incorporation of the drug 55 into the biocompatible polymer matrix 54 is shown as a plurality of small particles in the elution layer 52. In an embodiment of the present invention, the burst control layer 53 comprises the biocompatible polymer matrix 54 and the drug 55 incorporated into the biocompatible polymer matrix 54. In another embodiment of the present invention, the burst control layer 53 comprises the biocompatible polymer matrix 54 without the drug 55. Those skilled in the art will recognize the primer layer 51, the elution layer 52 and the burst control layer 53 can be comprised of combinations of the biocompatible polymer matrix and the drug and be within the spirit and scope of the present invention.

Figure 11:
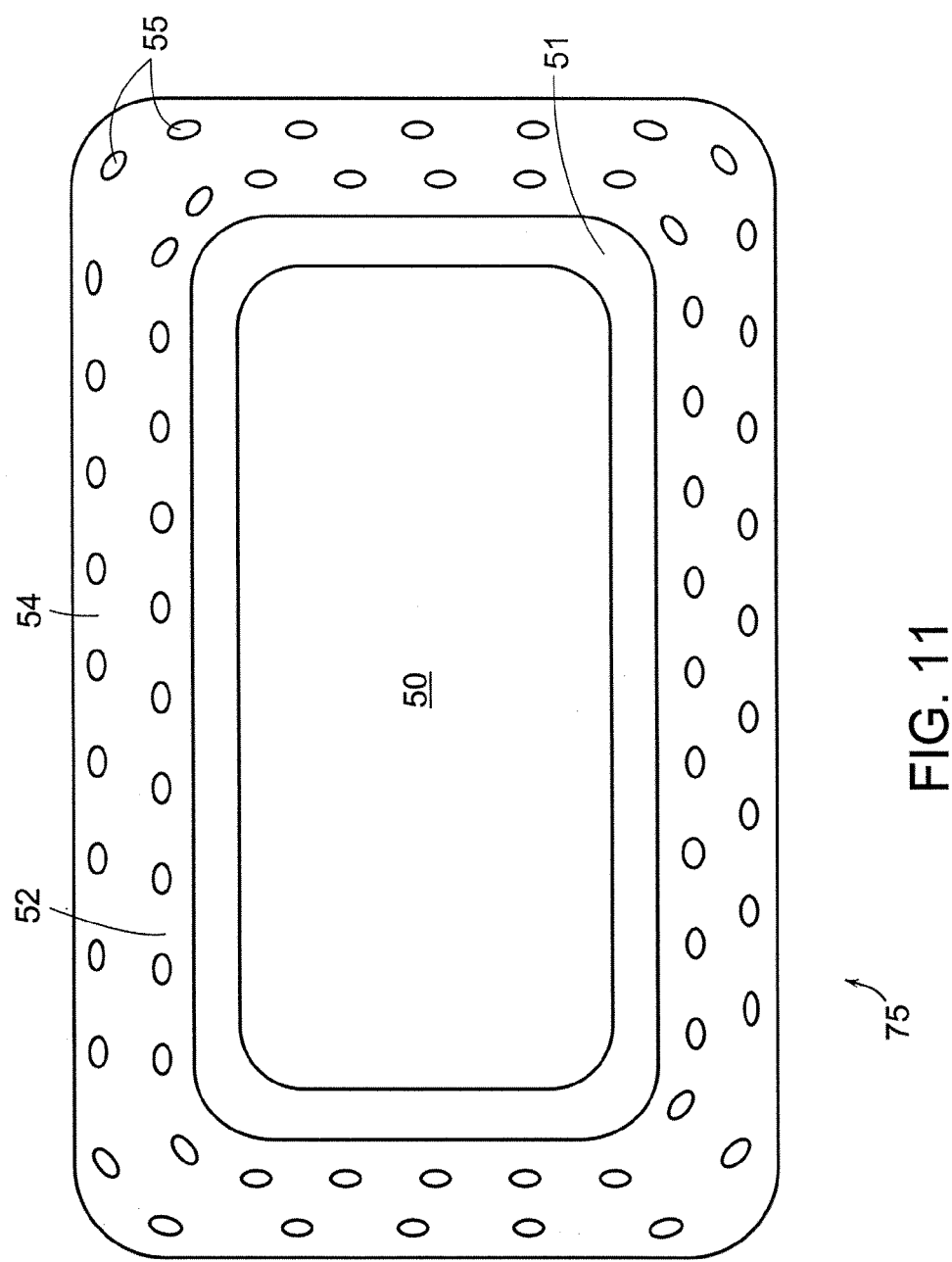
FIG. 11 is a cross section view of a strand of a biocompatible implantable medical device of the present invention with a strut surrounded by a first uniform coating layer and a second uniform coating layer.

Various embodiments of the strand 75 of the biocompatible implantable medical device 99 are contemplated in the present invention. The number of coating layers and composition of each coating layer may vary. FIG. 11 shows an alternative embodiment of the strand 75 of the biocompatible implantable medical device 99 of the present invention having the strut 50 surrounded by the primer layer 51 and the elution layer 52. The biocompatible drug release matrix of the elution layer 52 comprises the drug 55 embedded into the biocompatible polymer matrix 54. In one embodiment of the present invention, the primer layer 51 and the elution layer 52 are symmetric around the strut 50 and the primer layer 51 and the elution layer 52 have an equal and uniform thickness. In another embodiment of the present invention, the primer layer 51 and the elution layer 52 are asymmetric around the strut 50 and the primer layer 51 and the elution layer 52 vary in thickness. Those skilled in the art will recognize the layers surrounding the strand can be placed at various positions around the strut and be of varying thickness and be within the spirit and scope of the present invention.

Figure 13:
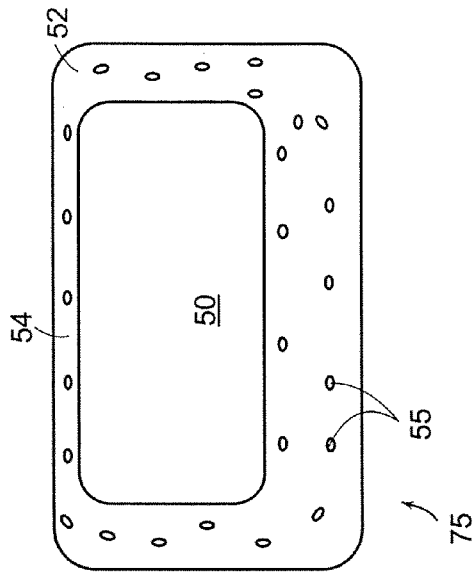
FIG. 13 is a cross section view of a strand of a biocompatible implantable medical device of the present invention with a strut surrounded by a single non-uniform coating layer.
Figure 12:
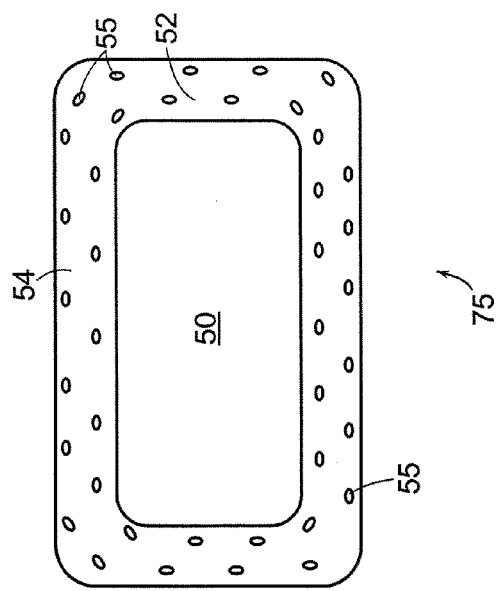
FIG. 12 is a cross section view of a strand of a biocompatible implantable medical device of the present invention with a strut surrounded by a single uniform coating layer.

FIG. 12 shows an alternative embodiment of the strand 75 of the biocompatible implantable medical device 99 of the present invention having the strut 50 surrounded by the elution layer 52. As shown in FIG. 12, the strut 50 is surrounded by a uniform thickness elution layer 52 positioned symmetrically around the strut 50. FIG. 13 shows an alternative embodiment of the strand 75 of the present invention with the strut 50 surrounded by a varying thickness elution layer 52 positioned asymmetrically around the strut 50.

In a preferred embodiment of the present invention, the strut 50 comprises a material allowing the biocompatible implantable medical device 99 to moved from an undeployed configuration (FIG. 1) to an expanded configuration (FIG. 21) without compromising the properties of the strut 50 or the adhesion between the primer layer 51, the elution layer 52 or the burst control layer 53. The strut 50 is comprised of a high strength material that maintains its material properties when the biocompatible implantable medical device 99 is moved from the undeployed configuration to the expanded configuration. Preferably, the strut 50 comprises a strong, flexible and biocompatible material. In a preferred embodiment of the present invention, the strut 50 comprises stainless steel or a stainless steel alloy. In an embodiment of the present invention, the strut 50 comprises stainless steel alloy 316L. In another embodiment of the present invention, the strut 50 comprises nitinol. Nitinol, also known as nickel titanium, is a shape memory alloy that exhibits superelasticity and high damping capability. Nitinol is a flexible, biocompatible material that allows the biocompatible implantable medical device 99 to be articulated through the tortuous paths of the vasculature, while providing high strength. The properties of nitinol can be modified by changes in alloy composition, mechanical working and heat treatment. In another embodiment of the present invention, the strut 50 comprises a material including, but not limited to gold, silver, copper, zirconium, platinum, titanium, niobium, niobium alloys, cobalt-chromium alloys or combinations of the above. Those skilled in the art will recognize the strut can comprise many other biocompatible materials known in the art and be within the spirit and scope of the present invention.

In an embodiment of the present invention, the strut 50 comprises a layer of tantalum or other radiopaque materials. Tantalum is a grayish silver, heavy metal that is biocompatible and has a history of uses in prosthetic devices. Tantalum is corrosion resistant, is immune to attack by body fluids and is radiopaque. The use of tantalum or other radiopaque materials provides enhanced radiographic imaging of the biocompatible medical device during implantation and subsequent fluoroscopic visualization.

In an embodiment of the present invention, the biocompatible polymer matrix 54 of the primer layer 51, the elution layer 52 and the burst control layer 53 have a similar composition. In another embodiment of the present invention, the biocompatible polymer matrix 54 of the primer layer 51, the elution layer 52 and the burst control layer 53 have a different composition. Those skilled in the art will recognize the biocompatible polymer matrix of the primer layer, the elution layer and the burst control layer can vary from one layer to the next and be within the spirit and scope of the present invention.

In an embodiment of the present invention, the drug 55 in the primer layer 51, the elution layer 52 and the burst control layer 53 have similar compositions. In another embodiment of the present invention, the drug 55 in the primer layer 51, the elution layer 52 and the burst control layer vary in composition. Those skilled in the art will recognize the drug in the primer layer, the elution layer and the burst control layers can vary from one layer to the next and be within the spirit and scope of the present invention.

In a preferred embodiment of the present invention, the primer layer 51 comprises a biocompatible polymer matrix 54 that improves the adhesion of the elution layer 52 to the strut 50. In a preferred embodiment of the present invention, the elution layer 52 comprises a biocompatible drug release matrix having a biocompatible polymer matrix 54 and the drug 55 incorporated into the biocompatible polymer matrix 54. In the embodiment shown in FIG. 10, the incorporation of the drug 55 into the biocompatible polymer matrix 54 is shown as a plurality of small particles in the elution layer 52. The burst control layer 53 controls and limits the kinetics of the burst dose of the drug 55 from the elution layer 52. In a preferred embodiment of the present invention, the elution layer 52 is symmetric around the strand 75 and has a uniform thickness. In another embodiment of the present invention, the elution layer 52 is asymmetric around the strand 75 and has a varying thickness. Those skilled in the art will recognize the layers surrounding the strut can be placed at various positions around the strut and be of varying thickness and be within the spirit and scope of the present invention.

In a preferred embodiment of the present invention, the concentration of the drug 55 in the burst control layer 53 is lower than the concentration of the drug 55 in the elution layer 52. With the concentration of the drug 55 in the burst control layer 53 lower than the concentration of the drug 55 in the elution layer 52 and the materials comprising the biocompatible polymer matrices of the burst control layer 53 and the elution layer 52 the same, the burst dosage of the drug 55 eluted to the tissue is slowed, leaving a higher amount of the drug 55 to elude after the lower burst dosage of the drug 55. With the concentration of the drug 55 in the burst control layer 53 lower than the concentration of the drug 55 in the elution layer, a lower amount of the drug 55 is diffused at the outer edges of the biocompatible implantable medical device 99. In another embodiment of the present invention, the concentration of the drug 55 in the burst control layer 53 is higher than the concentration of the drug 55 in the elution layer 52. With the concentration of the drug 55 in the burst control layer 53 higher than the concentration of the drug 55 in the elution layer 52, a higher burst dosage of the drug 55 is eluted to the tissue, leaving a lesser amount of the drug 55 to elude after the higher burst dosage of the drug 55. Those skilled in the art will recognize the concentration of the drug in the burst control layer can vary relative to the concentration of the drug in the elution layer and be within the spirit and scope of the present invention.

In an embodiment of the present invention, the primer layer 51, the elution layer 52 and the burst control layer 53 are comprised of a plurality of sub-layers applied sub-layer by sub-layer to produce the respective layer. In another embodiment of the present invention, the primer layer 51, the elution layer 52 and the burst control layer 53 are a single layer. In an embodiment of the present invention, the chemical composition of the plurality of sub-layers of the biocompatible polymer matrix 54 varies. In another embodiment of the present invention, the chemical composition of the plurality of sub-layers of the biocompatible polymer matrix is the same. In an embodiment of the present invention, the amount of the drug 55 incorporated into the biocompatible polymer matrix 54 varies from one sub-layer to the next sub-layer. In another embodiment of the present invention, the amount of drug incorporated into the biocompatible polymer matrix 54 is the same from one sub-layer to an adjacent sub-layer.

In an embodiment of the present invention, the biocompatible polymer matrix 54 comprises a single polymer. In another embodiment of the present invention, the biocompatible polymer matrix 54 comprises a plurality of polymers. Those skilled in the art will recognize the biocompatible polymer matrix can comprise one or several polymers and be within the spirit and scope of the present invention.

In an embodiment of the present invention, the biocompatible polymer matrix 54 comprises polyvinyl pyrrolidone (PVP) with at least one isocyanate. In another embodiment of the present invention, the biocompatible polymer matrix 54 comprises a polymer mixture of hydrophilic and hydrophobic polymers including, but not limited to, polyurethanes, polyvinyl pyrrolidone, poly methyl methacrylate (PMMA), hydroxyetyl methacrylate (HEMA) and cellulose esters. Bioactive agents are entrapped into the hydrophilic and hydrophobic polymer with the hydrophilic and hydrophobic polymers controlling the elution of the bioactive agent. In another embodiment of the present invention, the biocompatible polymer matrix comprises parylene and derivatives of parylene. Parylene and derivatives of parylene are appropriate for the burst control layer 53 because of parylene's biocompatibility, flexibility and ability coat complex geometry and small features evenly. Examples of polymers used in the biocompatible polymer matrix are found in U.S. Pat. No. 4,642,267; U.S. Pat. No. 5,069,899; U.S. Pat. No. 5,355,832; U.S. Pat. No. 5,447,799; U.S. Pat. No. 5,525,348; U.S. Pat. No. 5,997,517; U.S. Pat. No. 6,110,483; U.S. Pat. No. 6,306,176; U.S. Pat. No. 6,368,611; and U.S. Pat. No. 6,358,557, the entirety of these patents are hereby incorporated herein by reference.

In an embodiment of the present invention, the biocompatible polymer matrix 54 comprises polybutylmethacrylate and polyethylvinylacetate. In one embodiment of the present invention, the concentrations of polybutylmethacrylate and polyethylvinylacetate are approximately equal. In another embodiment of the present invention, the concentrations of polybutylmethacrylate and polyethylvinylacetate are not equal. In an embodiment of the present invention, the biocompatible polymer matrix 54 comprises a polyurethane-polycarbonate co-polymer. In an embodiment of the present invention, the biocompatible polymer matrix 54 comprises a thermoplastic polyurethane elastomer that exhibits characteristics including, but not limited to, low coefficient of friction, low extractables, dimensional stability, gamma sterilizable, chemical inertness, and biodurability. Such thermoplastic polyurethane elastomers are ChronoThane™ and ChronoFlex C™(commercially available from CardioTech International, Inc., Woburn, Mass. (www.cardiotech-inc.com)). In the embodiment of the present invention where the biocompatible polymer matrix 54 is the thermoplastic polyurethane elastomer, a ratio of the weight of the biocompatible polymer matrix and the drug is about 4 to about 1. Other ratios of the weight of the biocompatible polymer matrix 54 and the drug are possible and would be limited by the desired dosage of the drug 55 across the biocompatible implantable medical device 99, the resulting elution kinetics of the drug 55 and the amount of the biocompatible polymer matrix 54 required to yield the mechanical requirements for the particular layer to survive intact during the manufacture, implantation and long-term stability of the biocompatible implantable medial device 99.

In an embodiment of the present invention, the biocompatible polymer matrix 54 comprises an erodible polymer. Erodible polymers are non-permanent polymers that erode away over time while providing long-term biocompatibility. Erodible polymers reduce the risk of long-term breakdown of the biocompatible polymer matrix 54. The erodible polymer may be bioabsorbable polymers and resorbable polymers. Examples of erodible polymers include, but are not limited to, polyactide, polyactide with glycolide, polyester-amides, polyurethanes, poly(ethylene-urethane), poly(ester-urethane) and poly(ether-polyester-urethane), amino-acid based polyurethanes, polycaprolactone based polyurethanes, polyurethanes synthesized from poly(butylene succinate) polyol, poly(ethylene glycol), and 4,4'-methylenebis(cyclohexyl isocyanate), fat, carbohydrates, protein compounds and other natural biological substances. Those skilled in the art will recognize there are other erodible polymers known in the art that are within the spirit and scope of the present invention.

In another embodiment of the present invention, the biocompatible polymer matrix 54 includes, but is not limited to hybrid polymers, composites and polymer blends, hydrogels, acrylate terpolymers, tri-block polymers, polyethylene vinyl-acetate methacrylic tri-block terpolymer, ethyl-vinyl acetate, polyethyl vinyl-acetate, polybutyl methacrylic acid and polyethyl vinyl-acetate blends, polyurethanes and polyurethane-polycarbonate blends, silicone-urethane copolymers, polyvinyl pyrrolidone, polyester resins, parylene, lipids, sugars, gelatin, albumin and other biological materials. Those skilled in the art will recognize the biocompatible polymer matrix can be comprised of many materials known in the art and be within the spirit and scope of the present invention.

In an embodiment of the present invention, the drug 55 is stored within a plurality of perforations or reservoirs in the strut 50 of the biocompatible implantable medical device 99. The perforations or reservoirs allow for increased drug loading capability while focusing the release of the drug 55 toward the target cells. In addition, the perforations or reservoirs minimize the amount of the drug 55 lost in the blood stream. The perforations or reservoirs are placed in the strut 50 of the biocompatible implantable medical device 99 by laser drilling, casting, molding, machining or other methods known in the art.

In an embodiment of the present invention, the drug 55 is dissolved in a solvent and applied to the strut 50 of the biocompatible implantable medical device 99. After the solvent evaporates, the drug 55 will recrystallize on the surface of the strut 50. After recrystallization of the drug 55 on the surface of the strut 50, the burst control layer 53 may be applied to the surface of the strut 50. The burst control layer 53 can comprise the materials of the biocompatible polymer matrix 54 discussed herein.

The biocompatible drug release matrix is comprised of the biocompatible polymer matrix 54 and the drug 55. In one embodiment of the present invention, the drug 55 is added to the biocompatible polymer matrix 54 and mixed. In another embodiment of the present invention, the drug 55 is soaked into the biocompatible polymer matrix 54. Those skilled in the art will recognize the drug 55 can be incorporated into the biocompatible polymer matrix in many other ways known in the art and be within the spirit and scope of the present invention.

In a preferred embodiment of the present invention, a mixture of the biocompatible polymer matrix 54 and the drug 55 are mixed with a solvent. The choice of solvent affects the biocompatible drug release matrix, and more particularly, the interaction between the drug 55 and the biocompatible polymer matrix 54. In a preferred embodiment of the present invention, the solvent has low toxicity. The solvent is used to create a wet mixture of the biocompatible polymer matrix 54 and the drug 55 that can be deposited or applied to the surface of the biocompatible implantable medical device 99. The solvent allows for the mixing and a uniform distribution of the drug 55 in the biocompatible polymer matrix 54. The solvent evaporates, leaving the biocompatible polymer matrix 54 and the drug 55 on the strut 50 of the biocompatible implantable medical device 99. The drug 55 remains suspended within the biocompatible polymer matrix 54 on the surface of the strut 50. In a preferred embodiment of the present invention, the solvent used to mix with the biocompatible polymer matrix 54 and the drug 55 is water or saline. In another embodiment of the present invention, the solvents used to mix with the biocompatible polymer matrix 54 and the drug 55 include, but are not limited to, methanol, acetone, chloroform, tetrahydrofuran, ethanol, toluene, dimethyl sulfoxide, petroleum ethers, other hydrocarbons, butyl acetate, cyclohexanone, carbon tetrachloride, ether, benzene, organic solvents and other combinations of the above. Those skilled in the art will recognize other solvents known in the art can be used in the present invention that are within the spirit and scope of the present invention.

As described above, the biocompatible polymer matrix 54 (with or without the drug 55) for the primer layer 51, the elution layer 52 and the burst control layer 53 can comprise a plurality of sub-layers or a single layer. Many processes exist for applying the drug and the biocompatible polymer matrix 54 on the strut 50. Most processes for applying the biocompatible polymer matrix 54 involve direct application of the biocompatible polymer matrix 54. In addition, a secondary cycle may be required to fix the respective coating layer by evaporation of the solvent or an applied energy to bond, cure, polymerize or otherwise stabilize the respective coating layer. Processes used to apply the biocompatible polymer matrix 54 include, but are not limited to, brush coating, dip coating, spray coating, electrostatic deposition, ion sputtering, vapor deposition, chemical vapor deposition, pulsed chemical vapor deposition, controlled vacuum ultrasonic nanodrop spray deposition, flash evaporation and surface polymerization, polymer multi-layer deposition and combinations of the above. Those skilled in the art will recognize other methods of applying a biocompatible polymer matrix are known in the art and within the spirit and scope of the present invention.

In an embodiment of the present invention, the biocompatible drug release matrix coated on the surface of the biocompatible implantable medical device 99 is between about 5 microns to about 120 microns thick. Those skilled in the art will recognize the thickness of the biocompatible drug release matrix can vary and be within the spirit and scope of the present invention.

Figure 14:
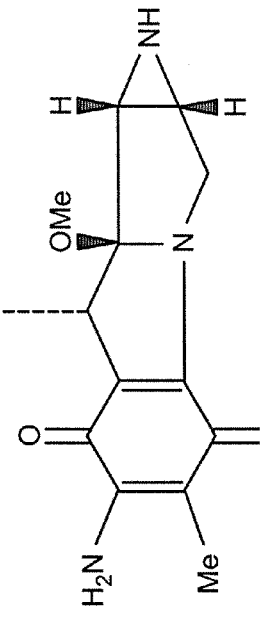
FIG. 14 is a chemical structure of mitomycin C.

In a preferred embodiment of the present invention, the drug 55 is mitomycin C. The chemical formula of mitomycin C is $C_{15}H_{18}N_4O_5$ and the chemical structure of mitomycin C is shown in FIG. 14. In another embodiment of the present invention, the drug 55 is an analogue related to the quinone-containing alkylating agents of the mitomycin family having anti-proliferative and antibiotic properties. In the present invention, the drug 55 may include, but is not limited to, mitomycin A, mitomycin A analogue 7-(2-hydroxyethoxy) mitosane (BMY 2551), mitomycin B, mitomycin C, KW-2149, BMS-191174, BMY 25282, BMY 25067, MC-77, MC-62, porfiromycin, acetylmitomycin C, FR-900482, FR-66979, FK-973, and combinations of the above. Those skilled in the art will recognize there are other derivatives, substitutes or analogues related to the mitomycin family known in the art are within the spirit and scope of the present invention.

Mitomycin is a quinone-containing alkylating agent with anti-proliferative and antibiotic properties. In addition, mitomycin is an alkylating agent that inhibits the DNA synthesis. Mitomycin is a chemotherapeutic antibiotic used for some types of cancer. Mitomycin effectively inhibits in-vitro proliferation of smooth muscle cells at various concentrations without adverse effects to a patient. Mitomycin is cytostatic at certain dosages and cytotoxic at different dosages.

In an embodiment of the present invention, the drug 55 is linked to a compound to alter the release kinetics, decrease the toxicity or enhance the potency of the drug 55. The compound to alter the release kinetics of the drug includes, but is not limited to, albumin, sodium chloride, chitosan, mannitol, heparin, steroids, glucose, glycoproteins, lipoproteins, estradiol, fibrin, antimitotics, and combinations of the above. Those skilled in the art will recognize the drug can be linked to other compounds known in the art to alter the release kinetics of the drug and be within the spirit and scope of the present invention.

The release kinetics and transport of the drug 55 can be altered by molecular bond degradation, a breakdown of the link of the drug 55 and the compound. The drug 55 may be covalently bonded to a the compound that acts as a carrier molecule. Typically, the drug 55 will not be active until the bond between the drug 44 and the carrier molecule breaks down through exposure to moisture (i.e., bodily fluids), exposure to heat or another applied energy source, or chemical triggers. For example, a systemic pharmaceutical trigger such as swallowing a pill, locally delivered pharmaceuticals via infusion catheter or locally delivering heat energy in the form of heat or light can affect the breakdown of the link of the drug 55 and the compound. Once the bond is broken down, the drug 55 is available to treat the surrounding tissue. The carrier molecule is selected to enhance or modify the diffusion properties of the drug 55, to alter the potency of the drug 55 and to provide extremely long elution rates of the drug 55. Linking the drug 55 to the compound might also decrease the toxicity of the drug 55, thereby altering the dosage of the drug 55.

Figure 15:
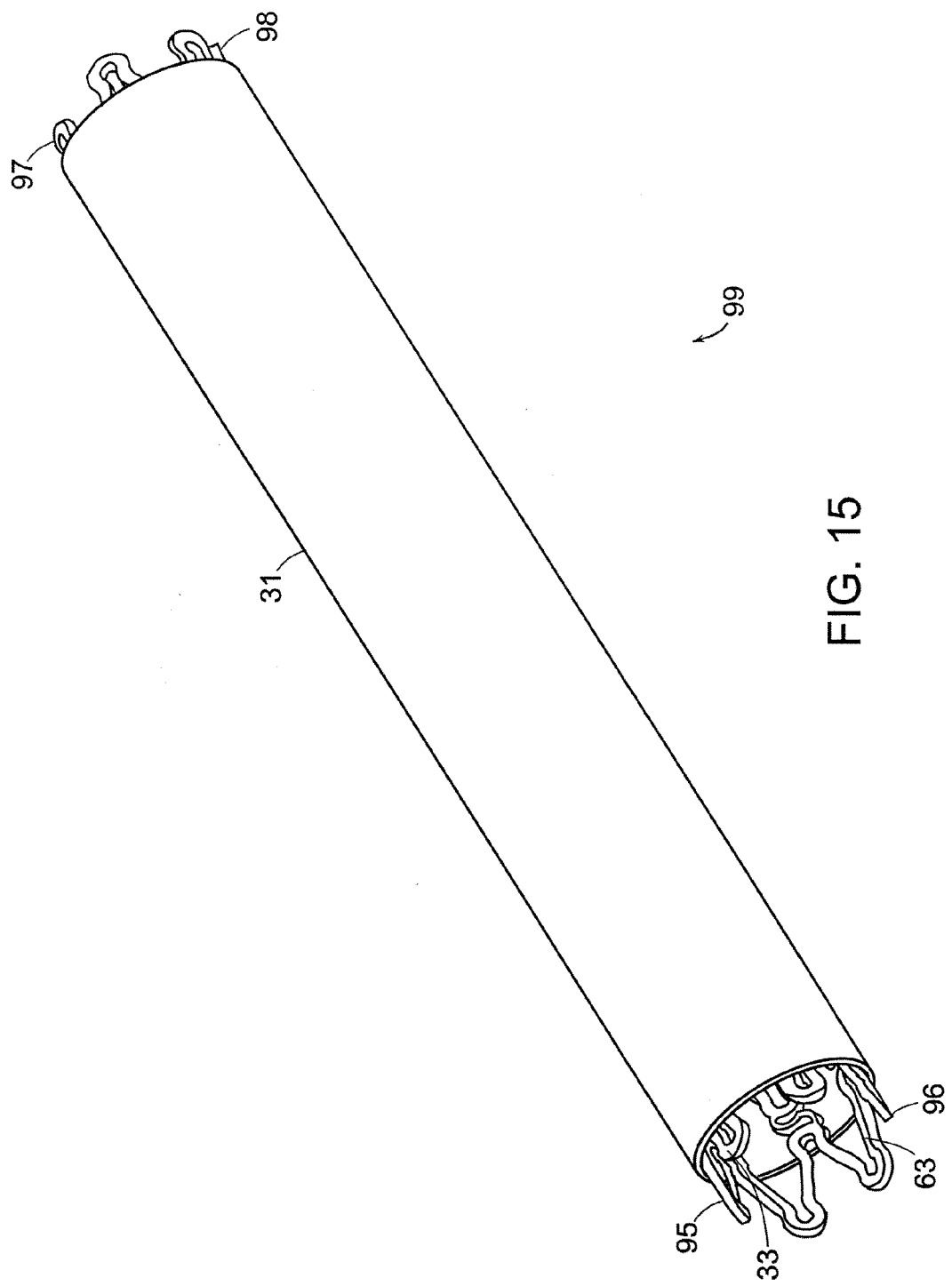
FIG. 15 is a perspective view of a biocompatible implantable medical device of the present invention with a film covering a portion of the biocompatible implantable medical device.
Figure 16:
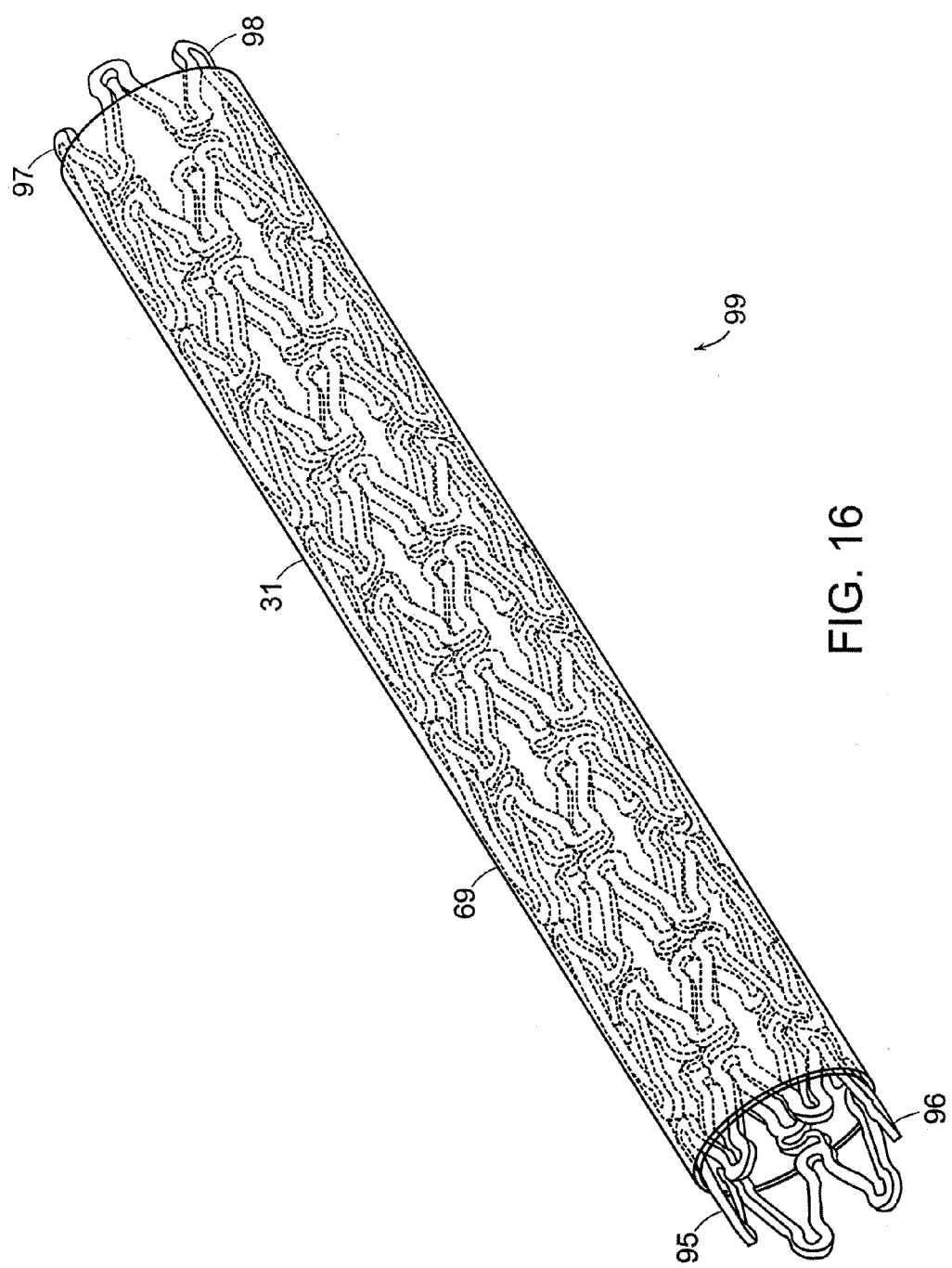
FIG. 16 is a perspective view of a biocompatible implantable medical device of the present invention with a film covering a portion of the biocompatible implantable medical device and showing the covered portion of the biocompatible implantable medical device.
Figure 17:
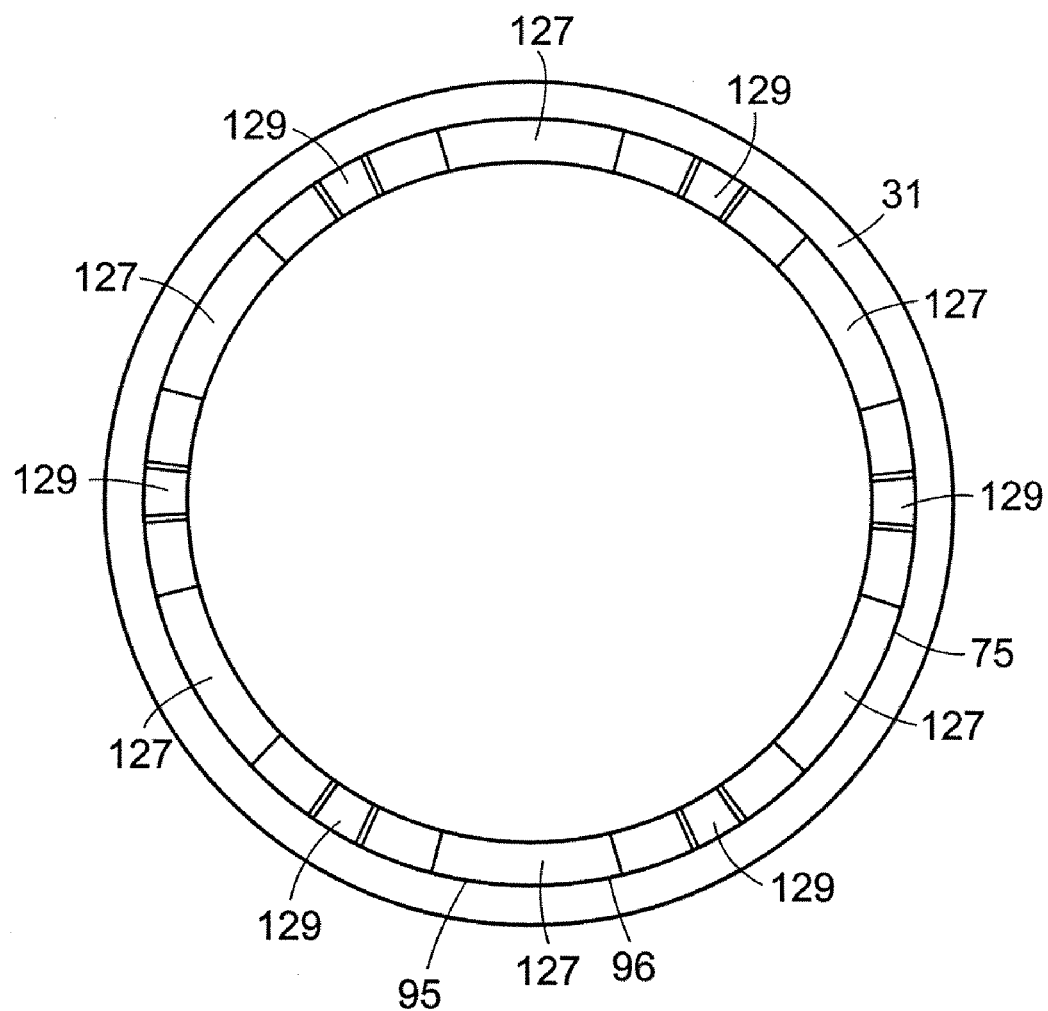
FIG. 17 is a front view of a biocompatible implantable medical device of the present invention with a film covering the biocompatible implantable medical device.

FIG. 15 shows the biocompatible implantable medical device 99 of the present invention having a film 31 of the biocompatible polymer matrix 54 and the drug 55 covering a portion of the biocompatible implantable medical device 99. FIG. 16 shows the biocompatible implantable medical device 99 of the present invention having the film 31 covering a portion of the biocompatible implantable medical device 99 with biocompatible implantable medical device 99 visible through the film 31. FIG. 17 shows a front view of the biocompatible implantable medical device 99 having the film 31 covering the biocompatible implantable medical device 99. In the embodiment of the present invention shown in FIG. 15, the film 31 comprising the biocompatible polymer matrix 54 and the drug 55 is applied to the primer layer 51. In another embodiment of the present invention, the film 31 comprising the biocompatible polymer matrix 54 and the drug 55 is applied to the strut 50. In the embodiment of the present invention shown in FIG. 15, the film 31 covers an outer surface 33 of the primer layer 51 between the proximal end 97 and the distal end 95 of the biocompatible implantable medical device 99. In another embodiment of the present invention, the film 31 covers an inner surface 63 of the primer layer between the proximal end 97 and the distal end 95 of the biocompatible implantable medical device 99. In another embodiment of the present invention, the film 31 covers the outer surface 33 of the primer layer 51 and the inner surface 63 of the primer layer between the proximal end 97 and the distal end 95 of the biocompatible implantable medical device 99.

The film 31 of the biocompatible implantable medical device 99 can be deposited or stretched over the strut 50 or the primer layer 51 of the biocompatible implantable medical device 99. In one embodiment of the present invention, the film 31 is deposited or stretched on the strut 50 or the primer layer 51 so the film 31 plastically deforms on an expansion of the biocompatible implantable medical device 99. A plastic deformation of the film 31 is a permanent deformation of the film 31 that prevents radial compressive forces from the film 31 transferring to the primer layer 51 and/or the strut 50 after expansion of the biocompatible implantable medical device 99. In another embodiment of the present invention, the film 31 expands elastically with the biocompatible implantable medical device 99. In one embodiment of the present invention, the film 31 comprises the same materials of the biocompatible polymer matrix 54 as discussed above. In an embodiment of the present invention, the film 31 is a porous structure comprised of the same materials as the biocompatible polymer matrix 54. In another embodiment of the present invention, the film 31 comprises the biocompatible polymer matrix 54 and the drug 55 to provide a more even distribution of the drug 55 over the outer surface 106 and inner surface of the biocompatible implantable medical device 99. In another embodiment, the covering consists of a plurality of films spaced along the length of the biocompatible implantable medical device 99 allowing for greater flexibility than a single film 31 alone.

Figure 18:
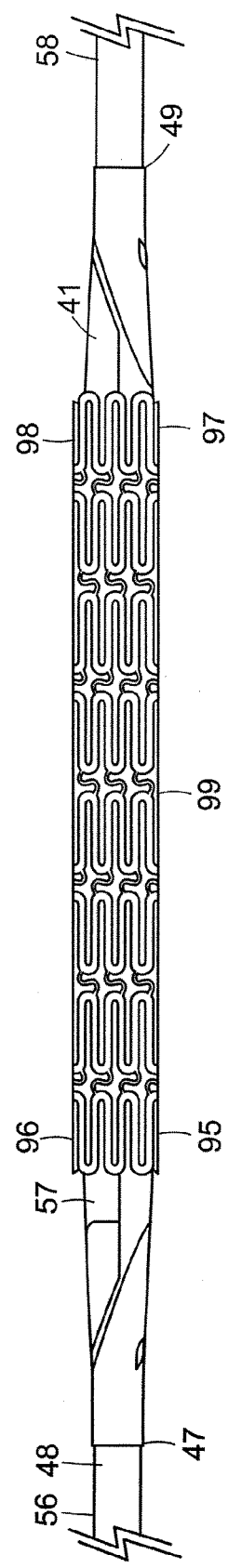
FIG. 18 is a side plan view of the present invention with a biocompatible implantable medical device engaged to a balloon of a balloon catheter.

FIG. 18 shows a side plan view of the biocompatible implantable medical device 99 of the present invention engaged on an outside surface 57 of a balloon 41 of a balloon catheter 48. In a preferred embodiment of the present invention, the biocompatible implantable medical device 99 is crimped onto the outside surface 57 of the balloon 41 of the balloon catheter 48. Crimping is performed to engage the biocompatible implantable medical device 99 onto the outside surface 57 of the balloon 41 through an interference fit. In one embodiment of the present invention, the biocompatible implantable medical device 99 is heated so the material comprising the balloon 41 softens around the biocompatible implantable medical device 99 to increase the retention forces between the balloon 41 and the biocompatible implantable medical device 99. High retention forces between the balloon 41 and the biocompatible implantable medical device 99 are desirable so the biocompatible implantable medical device 99 does disengage the balloon catheter 48 prior to the full expansion of the balloon 41. An inside surface of the biocompatible implantable medical device 99 engages the outside surface 57 of the balloon 41 of the balloon catheter 48. The balloon 41 of the balloon catheter 48 is supported by the balloon catheter 48 between a proximal end 58 of the balloon catheter 48 and a distal end 56 of the balloon catheter 48. The balloon 41 engages the balloon catheter 48 at an at least one engagement position along a longitudinal axis of the balloon catheter 48. In a preferred embodiment of the present invention, the balloon 41 engages the balloon catheter 48 at a distal engagement position 47 and a proximal engagement position 49 in a manner known in the art. In the embodiment of the present invention shown in FIG. 18, the balloon 41 is a tri-fold balloon.

The biocompatible implantable medical device 99 slides along the outer surface of the balloon catheter 48 and positioned over the balloon 41 of the balloon catheter 48. In a preferred embodiment of the present invention, the biocompatible implantable medical device 99 is centered with respect to the length span of the balloon 41. Once the biocompatible implantable medical device 99 is positioned with respect to the balloon, the biocompatible implantable medical device 99 is engaged onto the balloon 41 of the balloon catheter 48, causing an inner surface of the biocompatible implantable medical device 99 to engage to the outer surface 57 of the balloon 41 of the balloon catheter 48. The biocompatible implantable medical device 99 is engaged onto the balloon 41 of the balloon catheter in a manner known in the art. The diameter of the biocompatible implantable medical device 99 decreases after engaging the biocompatible implantable medical device 99 onto the outer surface 57 of the balloon 41 of the balloon catheter 48. The pliable, shape sustaining material that comprises the strut 50 of the biocompatible implantable medical device 99 provides flexibility for the biocompatible implantable medical device 99 to be moved from a larger diameter in an unengaged state to a smaller diameter in an engaged state.

The balloon catheter 48 is a small diameter hollow tube that is threaded through a vein or an artery of the vasculature. The balloon catheter 48 is a thin, flexible device that is used to deliver various medical devices to a treatment site in the vasculature. Various medical devices can be delivered through an inside of the balloon catheter 48 or along an outside surface of the balloon catheter 48. The balloon catheter 48 can be used to deliver fluids into the body or withdraw fluids from the body.

In a preferred embodiment of the present invention, the balloon catheter 48 comprises a strong, flexible and biocompatible material. In one embodiment of the present invention, the balloon catheter 48 comprises polytetrafluoroethylene (PTFE). In another embodiment of the present invention, the balloon catheter 48 comprises a material including, but not limited to, rubber, latex, silicone, PTFE, nylon, polyamide, polyethylene, polyurethanes, polyimide, stainless steel alloys, nickel-titanium alloy and similar materials. Those skilled in the art will recognize the balloon catheter may comprise many other materials known in the art and be within the spirit and scope of the present invention.

Figure 19:
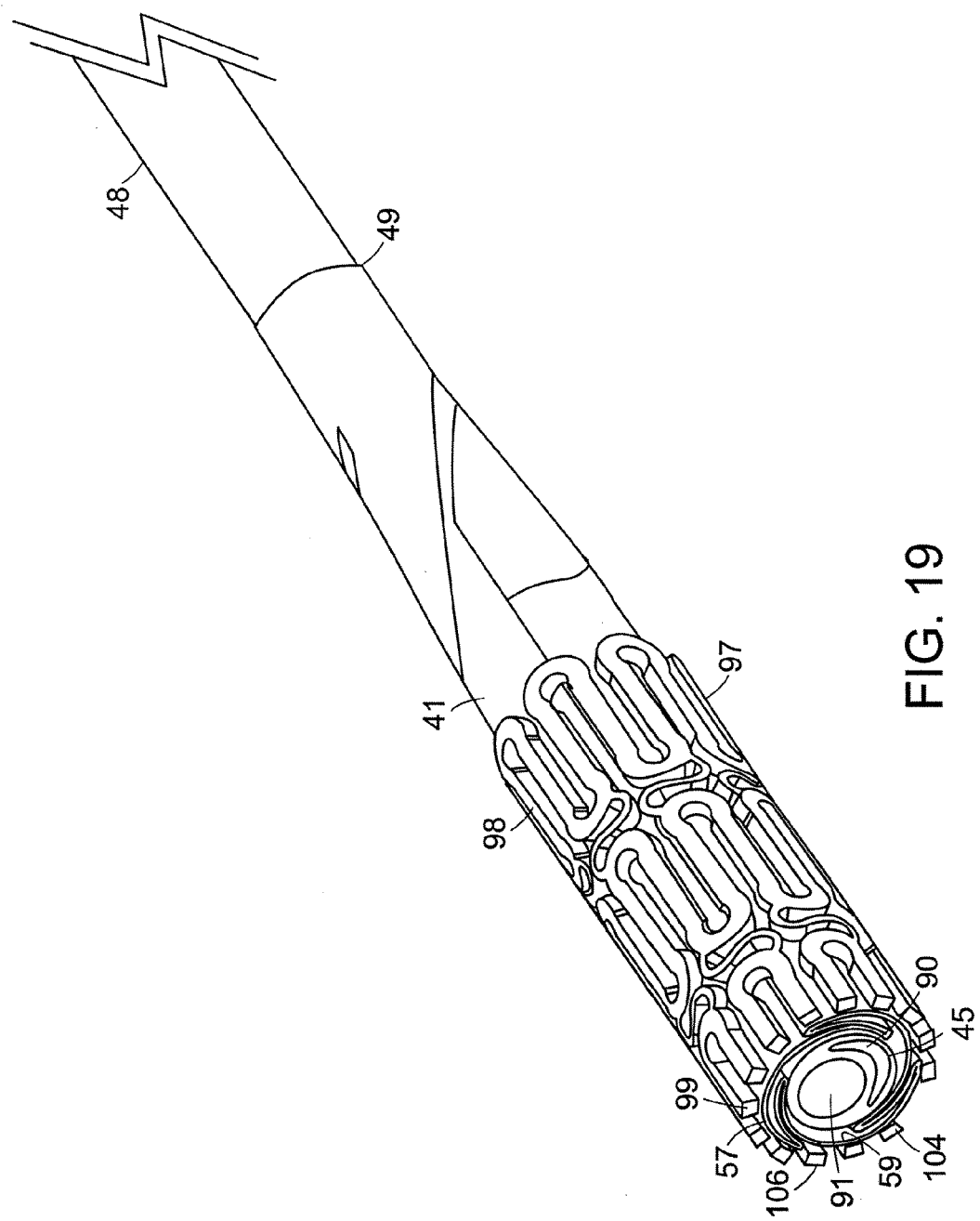
FIG. 19 is a fragmentary cross section perspective view of a biocompatible implantable medical device of the present invention and a balloon catheter.

FIG. 19 shows a fragmentary cross section perspective view of the biocompatible implantable medical device 99, the balloon 41 and the balloon catheter 48. In the embodiment of the present invention shown in FIG. 19, a cross section of the biocompatible implantable medical device 99 is simplified to illustrate the coating as a single layer as opposed to the individual primer layer 51, elution layer 52 and burst control layer 53. The biocompatible implantable medical device 99 comprises an outer surface 106 and an inner surface 104 engaged to the outer surface 57 of the balloon 41 of the balloon catheter 48. As discussed above, the biocompatible implantable medical device 99 comprises an at least one layer surrounding the strut 50. In a preferred embodiment of the present invention shown in FIG. 19, an inflation lumen 90 is located inside of the balloon catheter 48. In another embodiment of the present invention, the inflation lumen 90 is located outside of the balloon catheter 48. The balloon 41 of the balloon catheter 48 comprises the outer surface 57 and an inner surface 59. The balloon catheter 48 comprises a lumen extending along the longitudinal axis of the balloon catheter 48.

The inflation lumen 90 is used to deliver a medium from an inflation mechanism to inflate the balloon 41. The inner surface 59 of the balloon 41 is in communication with the inflation lumen 90. The medium is delivered from the inflation mechanism and moves along the inflation lumen 90 and out of an at least one inflation opening 45. As the medium is delivered, the medium engages the inner surface 59 of the balloon 41 and the balloon 41 expands.

In a preferred embodiment of the present invention, the medium is a liquid medium. In another embodiment of the present invention, the medium is water with a radiopaque contrast agent. In another embodiment of the present invention, the medium is saline. In another embodiment of the present invention, the medium is a gas. Those skilled in the art will recognize there are many media used to inflate a balloon known in the art that can be used and be within the spirit and scope of the present invention.

The balloon catheter 48 with the biocompatible implantable medical device 99 engaged onto the balloon 41 of the balloon catheter 48 is inserted into the vasculature 43. The balloon catheter 48 is moved within the vasculature to a treatment area comprising a lesion in the vasculature 43. In an embodiment of the present invention, the balloon catheter 48 is pushed to move the biocompatible implantable medical device 99 to the lesion. In another embodiment of the present invention, the balloon catheter 48 is twisted to move the biocompatible implantable medical device 99 to the lesion. In another embodiment of the present invention, the balloon catheter 48 is rotated within the vasculature to move the biocompatible implantable medical device 99 to the lesion. Those skilled in the art will recognize the balloon catheter can be moved within the vasculature in many ways known in the art and be within the spirit and scope of the present invention.

Figure 20:
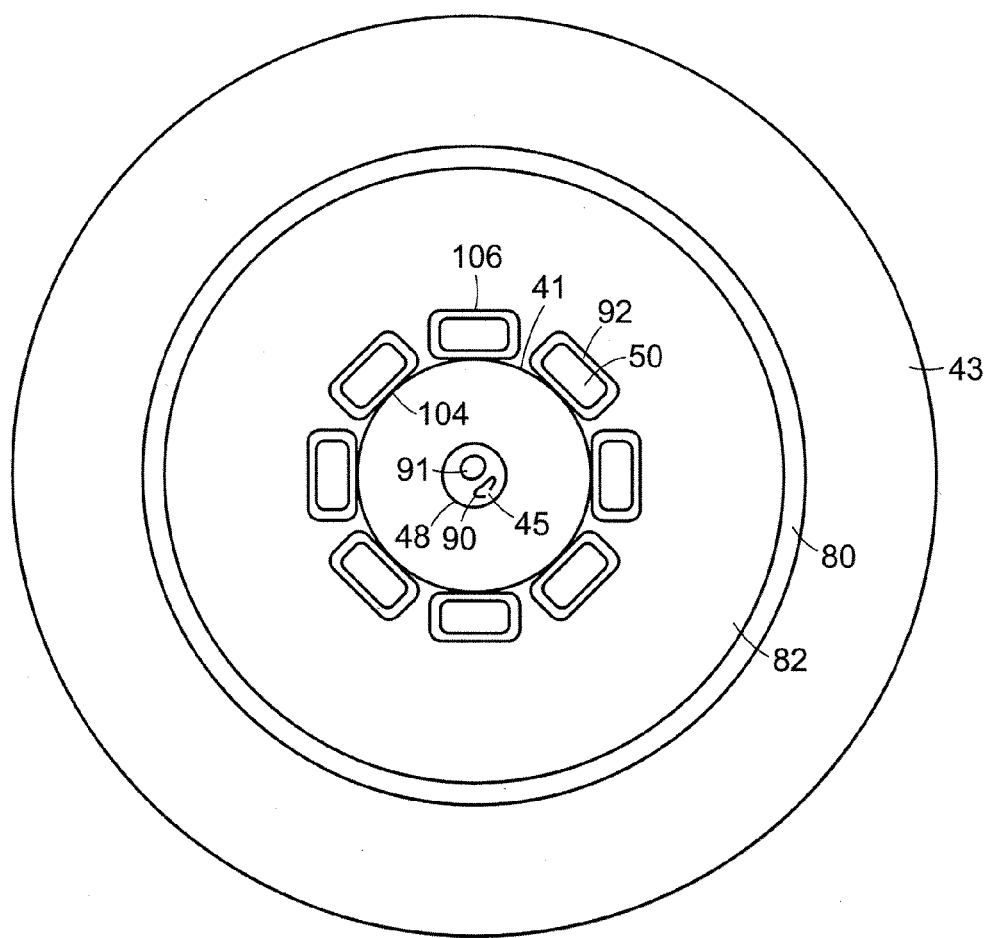
FIG. 20 is a cross section view of an inner wall of a vasculature in a body and a biocompatible implantable medical device of the present invention surrounding a balloon catheter with a balloon of the balloon catheter uninflated.

FIG. 20 shows a cross section view of the vasculature 43 of the body, a lesion 80 along an inner surface of the vasculature 43, the biocompatible implantable medical device 99 and the balloon catheter 48 after the biocompatible implantable medical device 99 is moved within a lumen 82 of the lesion 80 and positioned proximal to the lesion 80. FIG. 20 shows a vasculature after an angioplasty procedure is performed. The angioplasty procedure compresses the lesion 80 into the inside wall of the vasculature 43. In the embodiment of the present invention shown in FIG. 20, the balloon 41 is uninflated and the outer surface of the biocompatible implantable medical device 99 does not engage an inner surface of the lesion 80. In the embodiment of the present invention shown in FIG. 20, a cross section of the biocompatible implantable medical device 99 comprises the strut 50 surrounded by a matrix layer 92. In one embodiment of the present invention, the matrix layer comprises the primer layer 51, the elution layer 52 and the burst control layer 53. In another embodiment of the present invention, the matrix layer comprises the primer layer 51 and the elution layer 52. In another embodiment of the present invention, the matrix layer comprises the elution layer 52. Those skilled in the art will recognize the matrix layer can be comprised of various layers having various compositions and be within the spirit and scope of the present invention.

Figure 21:
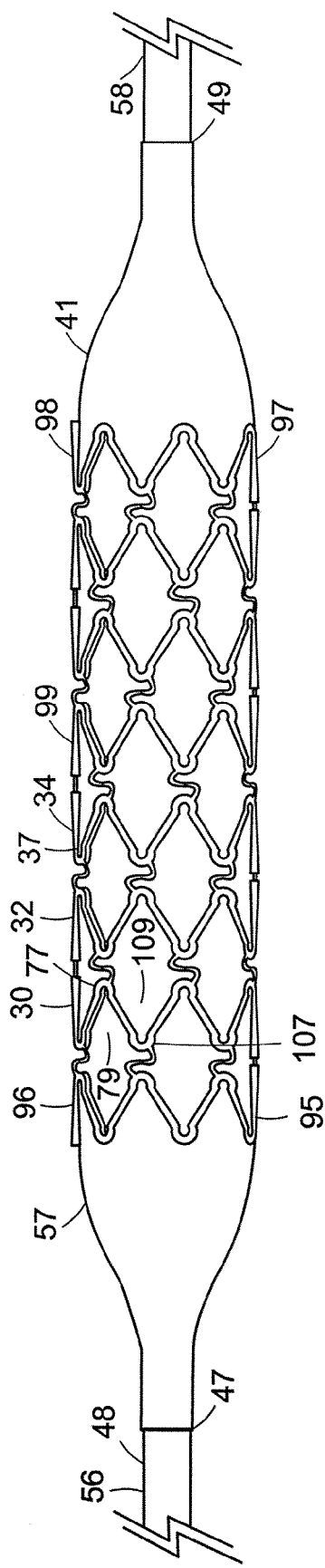
FIG. 21 is a side plan view of a biocompatible implantable medical device of the present invention in an expanded configuration with a balloon of a balloon catheter inflated.

FIG. 21 shows a side plan view of the biocompatible implantable medical device 99 in an expanded configuration after inflation of the balloon 41 of the balloon catheter 48. The construction of the biocompatible implantable medical device 99 of the present invention with the plurality of circumferential row of links 69 and the plurality of circumferential bands 37 allows the biocompatible implantable medical device 99 to be expanded from an undeployed configuration (FIG. 1) to the expanded configuration (FIG. 21). As the medium engages the inner surface 59 of the balloon 41, the balloon 41 inflates to a larger diameter causing the biocompatible implantable medical device 99 to expand in diameter with the inflated balloon 41. The biocompatible implantable medical device 99 increases from the smallest diameter corresponding to the biocompatible implantable medical device 99 engaged onto the uninflated balloon 41, to the diameter of the biocompatible implantable medical device 99 before the biocompatible implantable medical device 99 is engaged onto the balloon 41 of the balloon catheter 48, and finally to a largest diameter where the balloon 41 is inflated and the outer surface 106 of the biocompatible implantable medical device 99 engages the lesion 80.

In the embodiment of the present invention shown in FIG. 21, the plurality of circumferential bands 37 are expanded. The design of the biocompatible implantable medical device 99 with the plurality of flexible links 69 and the pliable, shape forming material comprising both the struts 50 and the plurality of links 69 allows the biocompatible implantable medical device 99 to expand to the configuration shown in FIG. 21. For the biocompatible implantable medical device 99 in the expanded configuration shown in FIG. 21, alternating bends within a circumferential band are spaced farther apart when compared to the configuration where the biocompatible implantable medical device 99 is engaged onto the balloon 41 of the balloon catheter 48 or the configuration of the biocompatible implantable medical device 99 before the biocompatible implantable medical device 99 is engaged onto the balloon 41 of the balloon catheter 48. For example, alternating bends 77 and 107 in circumferential band 30 are spaced further apart circumferentially than in the undeployed configuration shown in FIG. 4. The gaps 79 and 109 are spaced further apart circumferentially in the expanded configuration of FIG. 21. In addition, the plurality of circumferential links 69 allow for the biocompatible implantable medical device 99 to expand in a longitudinal direction.

Figure 22:
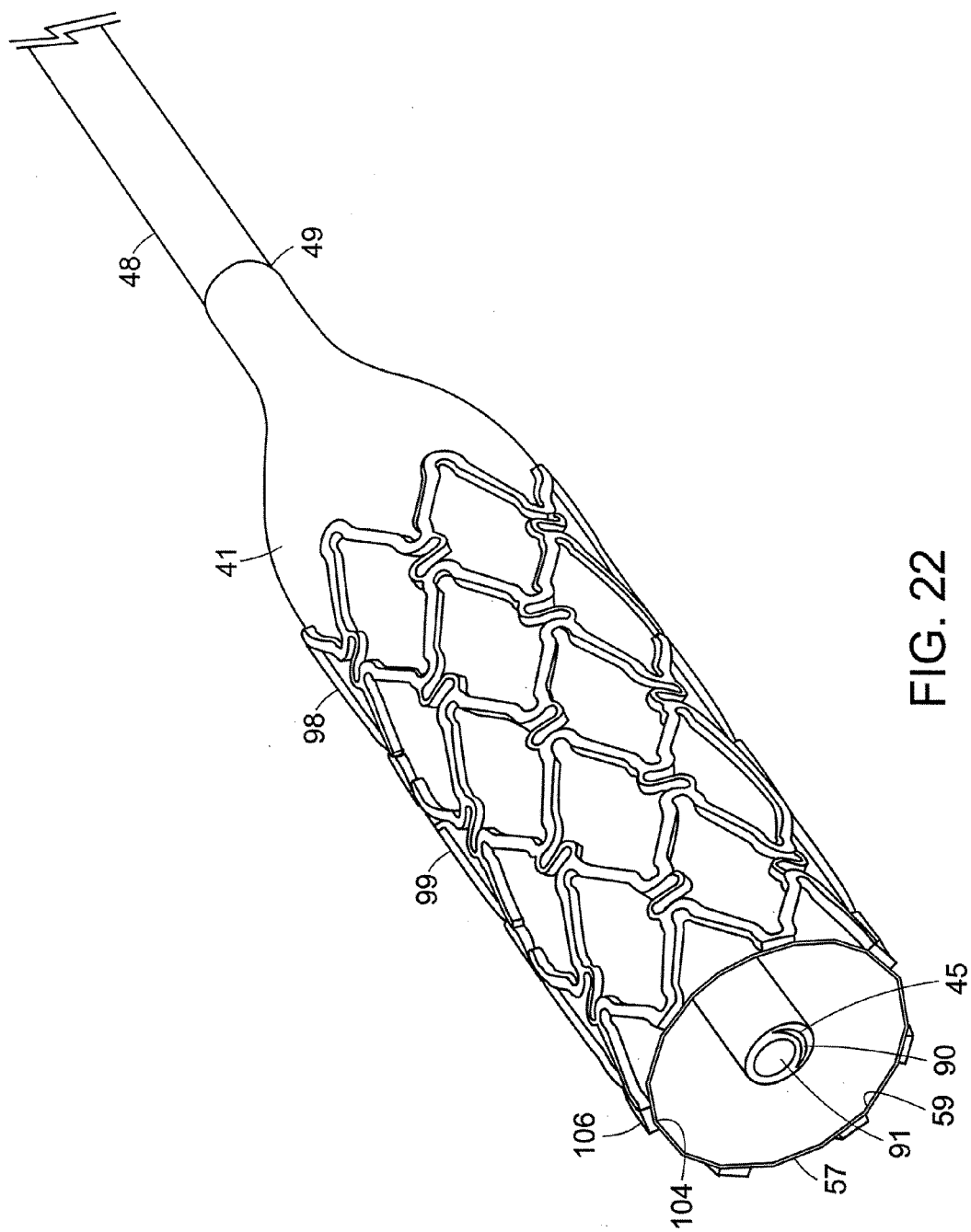
FIG. 22 is a fragmentary cross section perspective view of a balloon catheter and a biocompatible implantable medical device of the present invention in an expanded configuration.

FIG. 22 shows a fragmentary cross section perspective view of the biocompatible implantable medical device 99 in the expanded configuration, the inflated balloon 41 and the balloon catheter 48. In the embodiment of the present invention shown in FIG. 22, the tri-folds of the balloon 41 are expanded such that there is no overlap of the material comprising the balloon 41.

Figure 23:
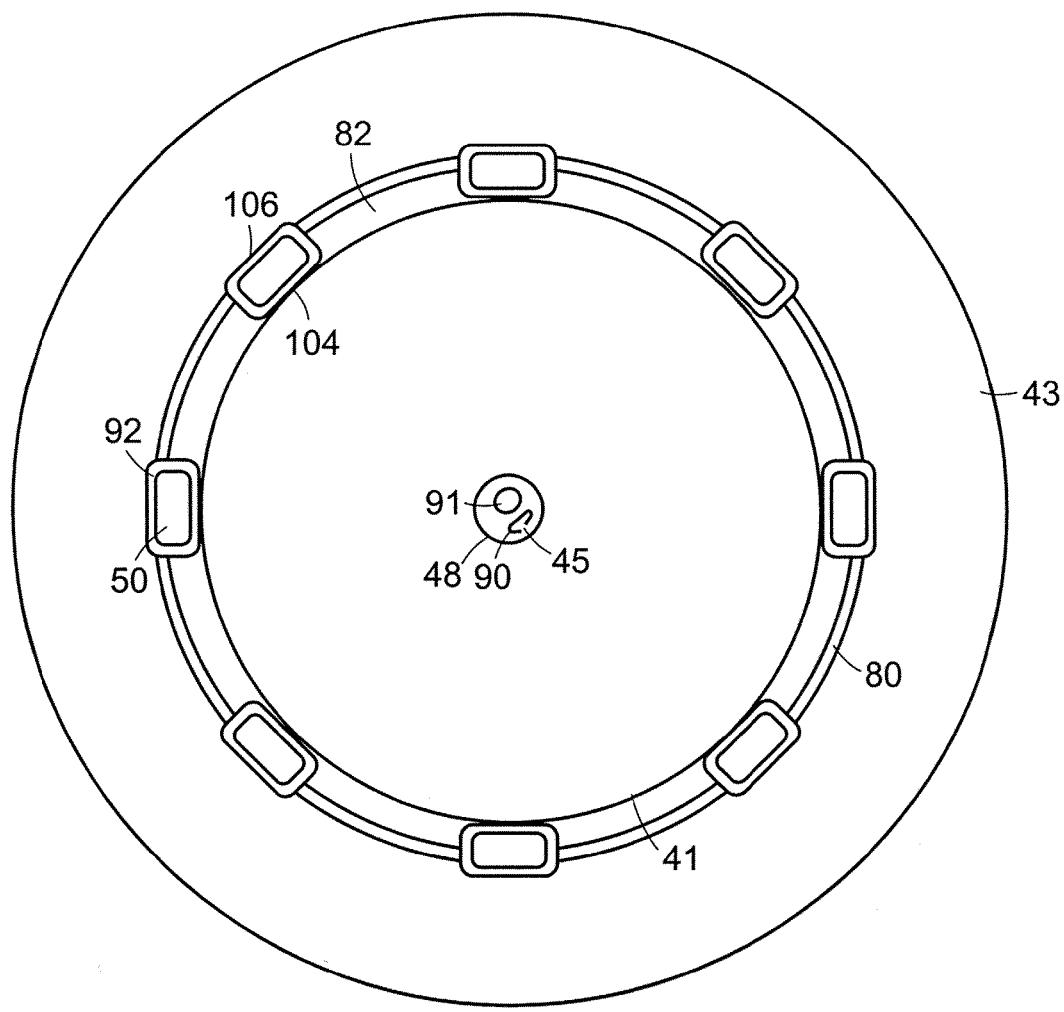
FIG. 23 is a cross section view of a biocompatible implantable medical device of the present invention engaging an inner wall of a vasculature in a body.

FIG. 23 shows a cross section view of the vasculature 43 and the lesion 80 with the biocompatible implantable medical device 99 in the expanded configuration, the inflated balloon 41 and the balloon catheter 48. The inflation of the balloon 41 expands the biocompatible implantable medical device 99 into the expanded configuration and pushes the biocompatible implantable medical device 99 adjacent to the compressed lesion and into the wall of the vasculature 43. The outer surface 106 of the biocompatible implantable medical device 99 engages the lesion 80 and compresses into the wall of the vasculature 43. In FIG. 23, the biocompatible implantable medical device 99 is implanted adjacent to the wall of the vasculature 43.

Figure 24:
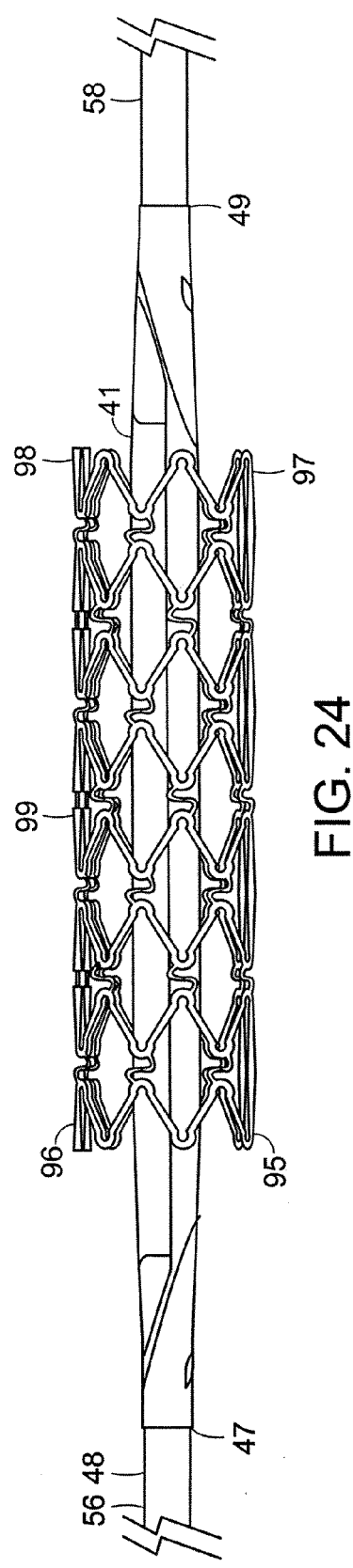
FIG. 24 is a side plan view of a biocompatible implantable medical device of the present invention in an expanded configuration and a balloon of a balloon catheter deflated.

FIG. 24 shows a side plan view of the biocompatible implantable medical device 99 in the expanded configuration and the balloon 41 of the balloon catheter 48 deflated. The balloon 41 of the balloon catheter 48 is deflated by removing the medium from within the balloon in a manner known in the art. Once the biocompatible implantable medical device 99 is implanted into the wall of the vasculature 43, the balloon 41 is deflated and the balloon catheter 48 with the balloon 41 is removed from the vasculature, leaving the biocompatible implantable medical device 99 implanted into the wall of the vasculature 43.

Figure 25:
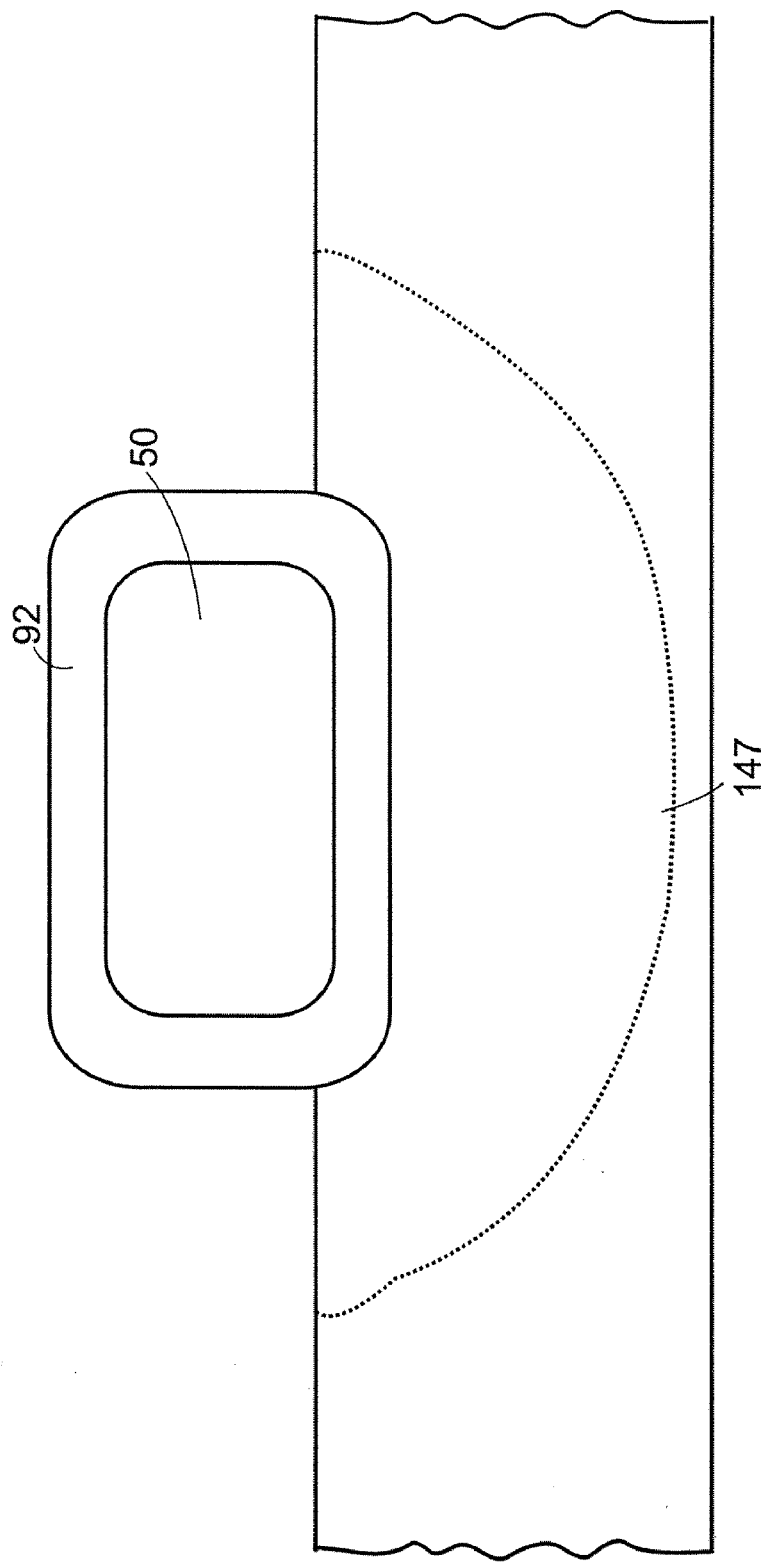
FIG. 25 is a cross section view of a strand of a biocompatible implantable medical device of the present invention engaging a wall of a vasculature, showing an effective treatment area of the wall of the vasculature.
Figure 26:
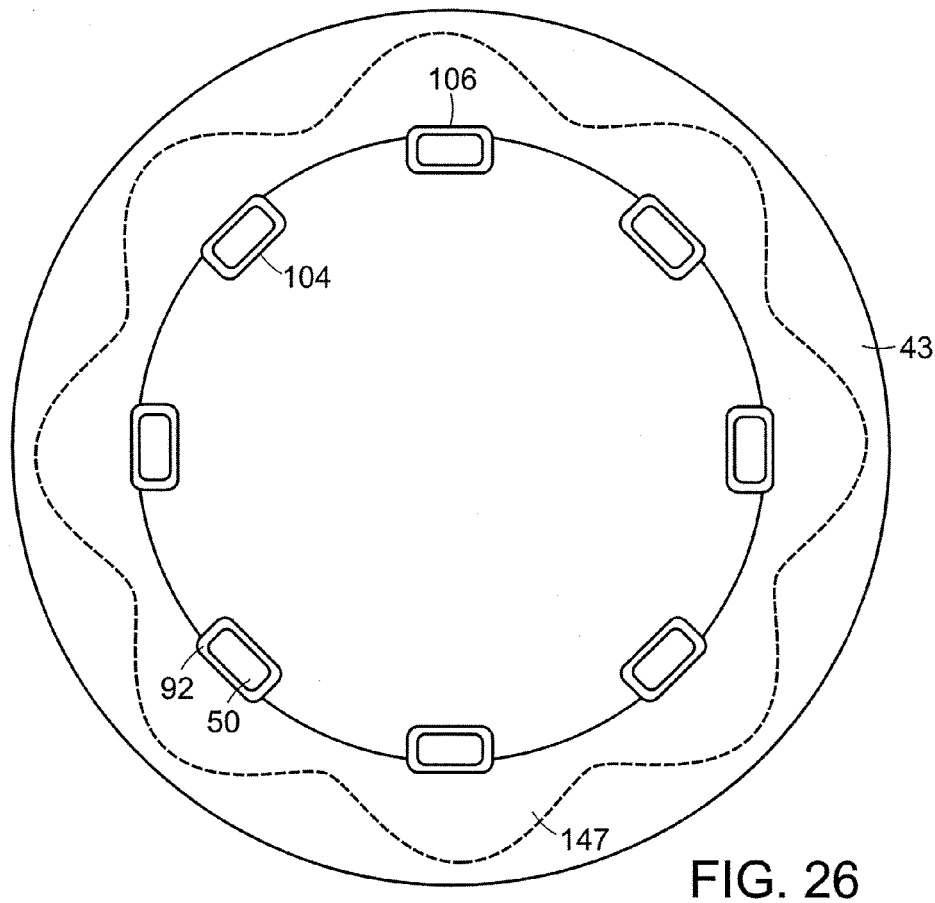
FIG. 26 is a cross section view of an effective treatment area of a wall of a vasculature in a body with a biocompatible implantable medical device of the present invention in an expanded configuration engaging the wall of the vasculature.

FIG. 25 shows a cross section view of the strand 75 of the biocompatible implantable medical device 99 of the present invention engaging a wall of the vasculature and a profile of the drug elution across the thickness of the wall. FIG. 26 shows a cross section of the vasculature with the implanted biocompatible implantable medical device 99 of the present invention engaging the inner wall of the vasculature. The treatment area 147 illustrates an effective treatment area of the drug 55. The concentration of the drug 55 is greater near the surface of the biocompatible implantable medical device 99 and decreases farther away from the surface of the biocompatible implantable medical device 99.

With the biocompatible implantable medical device 99 implanted into the wall of the vasculature 43, fluids engaging the biocompatible drug release matrix are transported into the biocompatible polymer matrix 54 and dissolve the drug 55 out of the biocompatible polymer matrix 54 to inhibit the proliferation of smooth muscle cells from the lesion 80. The fluid diffuses within the biocompatible polymer matrix 54 and dissolves the drug 55, therefore elution occurs and the drug 55 treats the smooth muscle cells from the lesion 80. The fluid transports out of the biocompatible polymer matrix 54 along with the drug 55 by virtue of a concentration gradient. The biocompatible polymer matrix 54 adds resistance to the transport of the fluid and slows the release of the drug 55. As the drug 55 moves out of the biocompatible polymer matrix 54 and is transferred to the vessel wall, the biocompatible polymer matrix 54 for the specific coating layer is left porous. The drug engages the smooth muscle cells of the lesion 80 along the vessel wall and inhibits the growth of the smooth muscle cells to keep the vasculature open.

The effectiveness of the inhibition of smooth muscle cell growth is a function of the total dose provided by the biocompatible implantable medical device 99 and the drug elution kinetics. The possibilities of loading an optimal therapeutic dose are limited by the total amount of drug that can be incorporated into the biocompatible polymer matrix 54. An inadequate amount of the drug 55 will not produce the desired effects of inhibiting restenosis, while an overabundance of the drug 55 can be toxic.

The total dose ($D_t$) can be described per the biocompatible implantable medical device 99, in micrograms per millimeter (μg/mm) of length of the biocompatible implantable medical device 99 or in micrograms per millimeter squared (μg/mm$^2$) of surface area of the biocompatible implantable medical device 99. After implantation of the biocompatible implantable medical device 99, the drug 55 is released based upon the properties of the biocompatible polymer matrix and the specific kinetics of the drug 55. The drug 55 moves through the surrounding tissues in the treatment area and results in a concentration within the tissue (measured in μg/mm$^3$ tissue, μg/ml of tissue or μg/mg tissue). The concentration of the drug within the tissue varies depending upon the distance from the strut 50 and the resistance from the various transport paths within the surrounding tissue.

The biocompatible polymer matrix 54 provides control over the rate of elution of the drug 55. For the drugs 55 entrapped in the biocompatible polymer matrix 54, the dissolution of the drug 55 is controlled by numerous factors including, but not limited to, the biocompatible polymer matrix/drug ratio (which can be adjusted), the total dose incorporated into the polymer matrix, characteristics of the polymer matrix, drug linking, the coating layers. The dissolution of the drug 55 may also be controlled by the ratio of hydrophilic to hydrophobic polymers within the biocompatible implantable medical device 99 with a higher amount of the hydrophobic polymer reducing the rate of diffusion of fluids within the biocompatible polymer matrix 54. The drug 55 at the outer coating surface dissolves away fairly easily, while the drug 55 deeper within the coating layer elutes more slowly. As discussed above, slower removal of the drug 55 results because the body fluid must first diffuse into the biocompatible polymer matrix 54, then the drug 55 must be dissolved and diffuse back out. The drug/biocompatible polymer matrix loading allows more of the drug 55 to be available sooner for release, and upon release leaves more voids in the biocompatible drug release matrix for faster diffusion and penetration of fluids into deeper structures of the biocompatible polymer matrix 54. The burst control layer 53 acts as a restriction to further reduce the rate of diffusion in and out of the elution layer 52.

The drug elution kinetics are dependent upon various factors including, but not limited to, the type and amount of the drug 55 used, the type and amount of biocompatible polymer matrix 54, the type and amount of solvent used and the use of the burst control layer 53. For example, the drug elution kinetics profile is dependent upon the thickness of the coating layer, the ratio of the drug 55 to the biocompatible polymer matrix 54, the ration of hydrophilic to hydrophobic polymers, the compatibility of the drug 55 and the biocompatible polymer matrix 54 and the solubility of the drug 55. Due to losses of the drug 55 from the treatment area through diffusion of the drug 55 into the blood and surrounding tissues, or inactivation of the drug 55 from exposure to proteins, it is difficult to predict the exact dosage of the drug 55 and the drug elution kinetics for the biocompatible implantable medical device 99. However, tissue deposition studies are used to adjust the drug elution kinetics and dosage of the drug 55 to provide the desired biological effect of inhibition of the proliferation of smooth muscle cells. In general, the drug elution kinetics is affected by the amount of the drug 55 in the biocompatible polymer matrix 54. The higher the amount of the drug 55 relative to the biocompatible polymer matrix 54, the higher the amount of drug elution since there is more of the drug 55 to dissolve and more vacancies in the biocompatible polymer matrix 54 for the diffusion to occur.

One example of a study was conducted to investigate the vascular smooth muscle cell proliferation (VSMC) from varying concentrations of the mitomycin C. The results of the study, demonstrated about 66% of the VSMC are inhibited with a dose of about 0.334 micrograms per milliliter, while about 98% of the VSMC are inhibited under a dose of about 25.1 micrograms per milliliter. An extrapolation from a logarithmic curve defined by points of the VSMC at various dosages of mitomycin C suggests that about 50% VSMC inhibition occurs at approximately 0.067 micrograms/milliliter of mitomycin C. A lower dosage of mitomycin C would still permit the advance of VSMC and contribute to increased restenosis and may be sufficient. Depending upon the observed biological effects from potentially cytotoxic local tissue levels, a higher concentration of mitomycin C may also still be sufficient.

The drug elution kinetics should yield tissue concentration levels in the desired range during the healing cycle where smooth muscle cell activation and growth occurs. The proliferative phase of smooth muscle cell growth decreases after about fourteen days after the initial treatment (i.e. angioplasty procedure). In one embodiment, it may be desirable to yield a quicker burst dose of the drug 55 in the first few days (i.e., twenty-four to seventy-two hours) and then sustain a slow and steady level release of the drug 55 beyond the proliferative cycle, in a time as much as forty-five to sixty days from implant, to further protect against restenosis.

The use of the burst control layer 53 also affects the drug elution kinetics. The burst control layer 53 acts as a restriction to limit the diffusion of the drug 55 out of the elution layer 52 and burst control layer 53. In many cases, a large amount of the drug 55 is diffused from the biocompatible polymer matrix 54, thereby inhibiting the proliferation of smooth muscle cells with a large dosage of the drug 55 immediately. Over time as the smooth muscle cells proliferate, there is less of the drug 55 available to effectively inhibit the proliferation of smooth muscle cells, increasing the possibility for restenosis to occur. In particular, the burst control layer 53 with the biocompatible polymer matrix 54 absent of the drug 55 is used to reduce the initial dump of the drug 55 from the biocompatible polymer matrix 54. In addition, the burst control layer 53 comprising the biocompatible polymer matrix 54 and an amount of the drug 55 can also affect the drug elution kinetics.

In a preferred embodiment of the present invention, the biocompatible implantable medical device is designed so between about 10% and about 60% of the drug 55 is delivered to the lesion 80 in the first few days after implantation of the biocompatible implantable medical device 99. By allowing between about 10 percent and about 60 percent of the drug 55 to be delivered to the lesion 80 in the first few days after implantation, the remainder of the drug 55 is allowed to slowly diffuse out over time to effectively inhibit restenosis.

Figure 27:
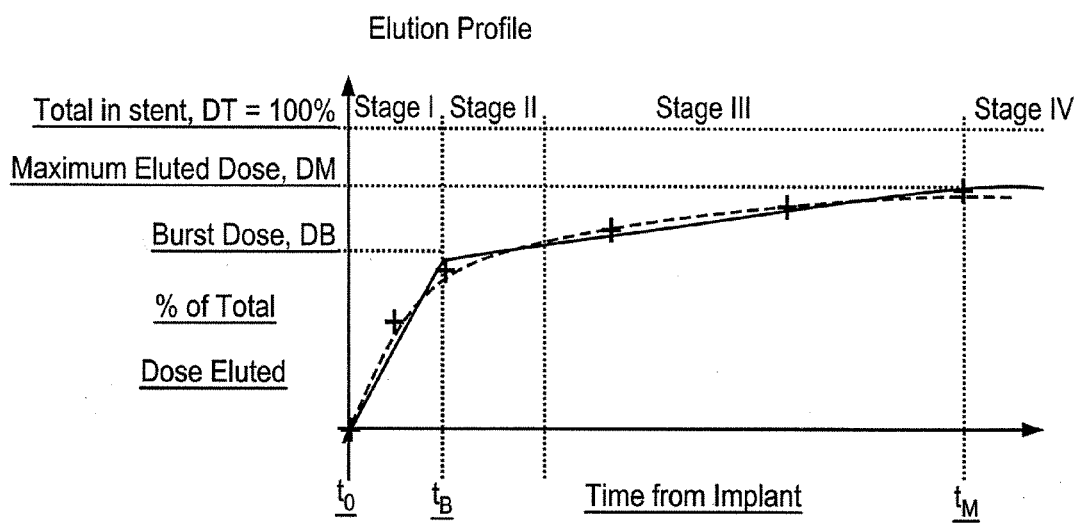
FIG. 27 is an elution profile of mitomycin C showing the release of mitomycin C from a coating of a biocompatible implantable medical device of the present invention as a function of time.

FIG. 27 shows an elution profile of mitomycin C showing the release of mitomycin C from a coating of a biocompatible implantable medical device 99 of the present invention as a function of time. The vertical axis represents the percent of the drug 55 eluted to the tissue while the horizontal axis represents the time from implantation of the biocompatible implantable medical device 99. Treatment using the present invention can be viewed as four stages of drug elution that may require a variable amount of the drug 55 to achieve the desired effect. Upon implantation ($t_O$) of the biocompatible implantable medical device 99, there is an initial burst of the drug, $D_B$, (Stage I) or a rapid release within about the first one to three days of exposure, $t_B$, followed by a period of sustained release of the drug 55. The smooth muscle cell proliferation cycle during healing typically peaks at about two weeks and inhibition of the smooth muscle cells during this time period (Stage II) is essential. Late term elution (Stage III) occurs after the two weeks and is characterized by residual elution of the drug 55. Over the period of sustained release ($t_m$), an addition amount of the drug 55 is eluted from the biocompatible implantable medical device 99, shown as $D_M$ in FIG. 27. Late term elution of the drug 55 beyond the first two weeks after implantation my beneficially inhibit smooth muscle cell proliferation. Stage IV begins when there is no drug 55 on or eluting from the biocompatible implantable medical device 99. As discussed previously, the amount of the drug 55 eluted from the FIG. 27, is typically less than the amount of the drug 55 in the biocompatible implantable medical device, shown as $D_T$ in FIG. 27.

Figure 28:
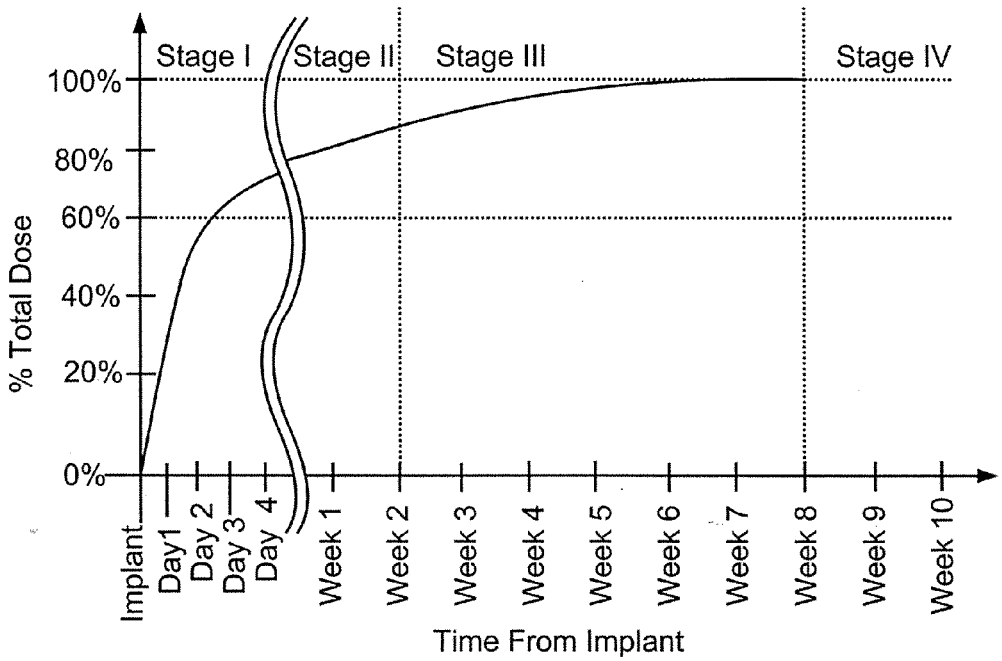
FIG. 28 is an elution profile of mitomycin C showing a high burst dosage (about 60%) of the drug followed by a slow release of the drug (about 8 weeks).
Figure 29:
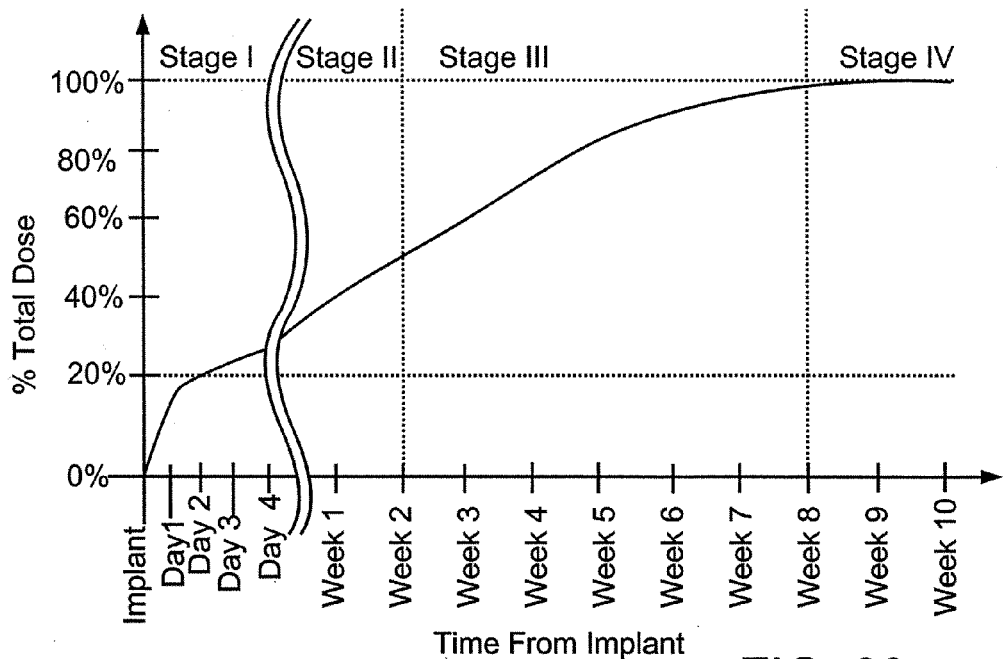
FIG. 29 is an elution profile of mitomycin C showing a low burst dosage (about 20%) of the drug followed by a slow release of the drug (about 8 weeks).
Figure 30:
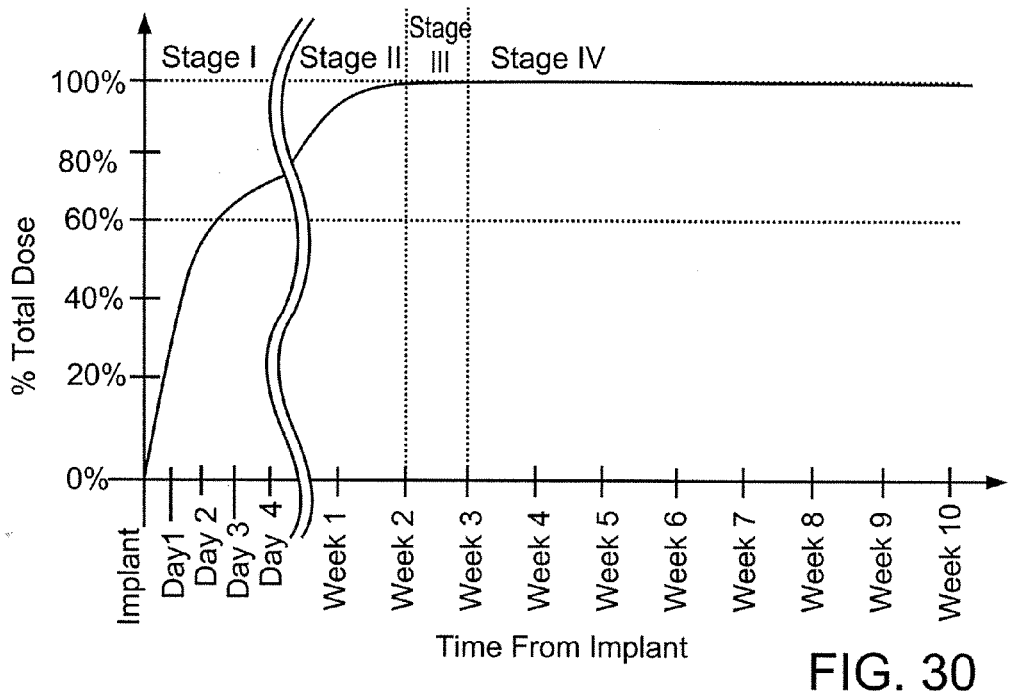
FIG. 30 is an elution profile of mitomycin C showing a high burst dosage (about 60%) of the drug followed by a fast release of the drug (about 3 weeks).
Figure 31:
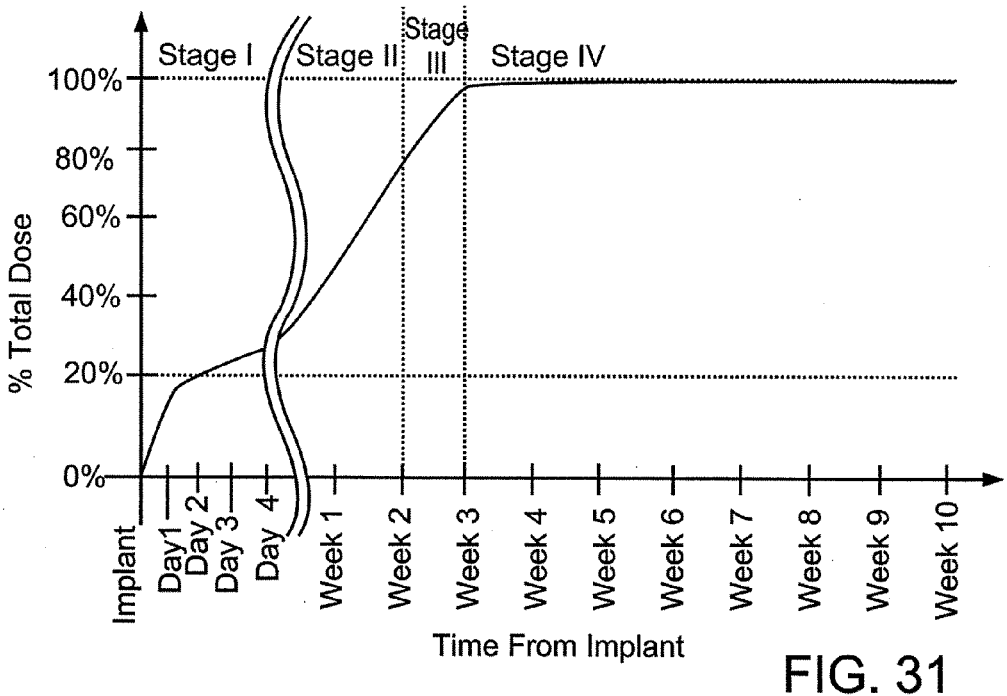
FIG. 31 is an elution profile of mitomycin C showing a low burst dosage (about 20%) of the drug followed by a fast release of the drug (about 3 weeks).

As discussed above, the drug release kinetics can be tailored to alter the burst dosage and the sustained release of the drug 55. FIG. 28 shows an elution profile of mitomycin C illustrating a high burst dosage (about 60% total dose elution) followed by a slow release of the drug 55 over about eight weeks. FIG. 29 shows an elution profile of mitomycin C illustrating a low burst dosage (about 20% total dose elution) followed by a slow release of the drug 55 over about eight weeks. FIG. 30 shows an elution profile of mitomycin C illustrating a high burst dosage (about 60% total dose elution) followed by a fast release of the drug 55 over about three weeks. FIG. 31 shows an elution profile of mitomycin C illustrating a low burst dosage (about 20% total dose elution) followed by a fast release of the drug 55 over about three weeks.

In an embodiment of the present invention, a total dosage of about 10 micrograms of the drug per millimeter of a length of the biocompatible implantable medical device 99 is coated on the biocompatible implantable medical device 99. In another embodiment of the present invention, a total dosage of between about 0.5 and about 50 micrograms of the drug per millimeter of length of the biocompatible implantable medical device 99 is coated on the biocompatible implantable medical device 99. Those skilled in the art will recognize that the dosage of the drug per millimeter of a length of the biocompatible implantable medical device can vary and be within the spirit and scope of the present invention. An example calculation of the total dosage of the drug is shown below for several loss factors.

An analytical method of calculating the dosage of the drug 55 on the biocompatible implantable medical device 99 is given by Equation 1 as follows:

$$D_T = \frac{1}{X} \cdot C \cdot T \cdot V = \frac{1}{X} \cdot C \cdot T \cdot L_v \cdot \frac{\pi}{4}((D+2t)^2 - D^2) = \frac{1}{X} \cdot C \cdot T \cdot L_v \cdot \pi \cdot t \cdot (D+t) \quad (1)$$

Equation 1 is a first order approximation of the total dose of the drug 55 assuming a daily consumption rate of the drug 55. In Equation 1, $L_v$ is the treated length of the biocompatible implantable medical device 99, t is an effective treatment penetration depth, T is a constant elution time, C is a desired inhibitory concentration, V is a treated tissue volume, and X is the loss factor. For an L (Length)=13 mm long stent expanded to D (Diameter)=4.0 mm, an effective treatment penetration depth of t=1.5 mm, a constant (steady) elution for T=45 days maintaining a desired inhibitory concentration of C=0.667 μg/ml per day, the following relationship between total dosage an loss factor can be estimated as:

$$D_T = \frac{1}{X} \cdot 0.667 \frac{\mu g}{ml \cdot day} \cdot 45 \text{ days} \cdot$$
$$17 \text{ mm} \cdot \pi \cdot 1.5 \text{mm} \cdot (4.0 \text{ mm} + 1.5 \text{ mm}) \cdot \frac{1 \text{ ml}}{1000 \text{ mm}^3} = \frac{13.2 \text{ μg}}{X}$$

The loss factor, X, is a sum of the losses from direct diffusion of the drug 55 into the bloodstream, both during insertion and immediately after implantation, as well as losses resulting from the drug 55 trapped in the biocompatible polymer matrix 54 permanently (typically less than 10% of the total dosage loss). It is also possible to incorporate non-linearity of the elution rate within the loss factor. Using the above equation with loss factors ranging from 1% to 100%, the total dose of the drug is calculated with the results listed in FIG. 32.

Figure 33:
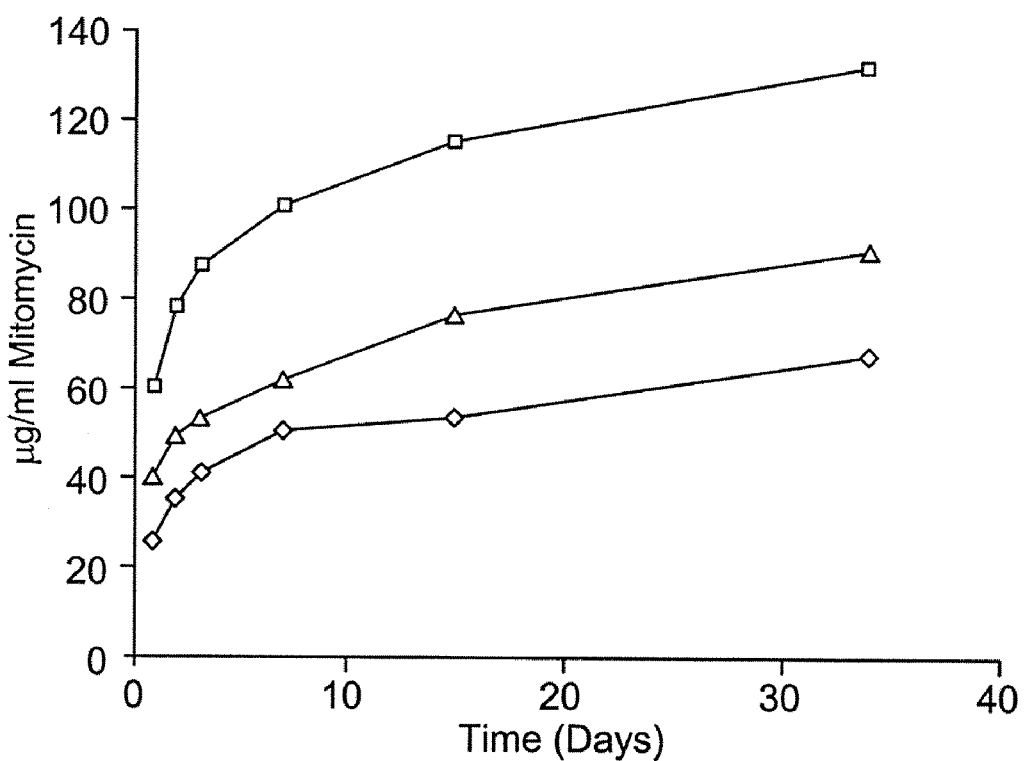
FIG. 33 is a graph showing release of mitomycin C from a polymer stent coating stent delivered up to a forty day time period.

FIG. 33 shows a graph showing release of mitomycin C from a polymer stent coating stent delivered up to a forty day time period. The clinical data that forms FIG. 33 comes from a study of biocompatible implantable medical devices (stents) of the present invention implanted into porcine coronary arteries to analyze neointimal formation. The stent included a biocompatible polymer having polybutylmethacrylate (PBMA) and polyethylenevinylacetate (PEVA) in equivalent concentrations (1:1) co-solubilized with mitomycin C in a suitable solvent. The solution was then deposited via nebulizer onto a stent, where a homogeneous drug delivery matrix was formed by solvent evaporation. The dose of mitomycin was about 200 mcg per stent corresponding to about 20% loading rate. Thus, the total mass of the coating including drug was between about 1800 mcg and about 2000 mcg.

The drug release profile kinetics of mitomycin C release from the polymer used for stent coating was determined, in vitro, using the drug assay. Drug/polymer coated stents were placed in physiologic buffer solution at 37° C. in a rotating incubator bath. Buffer samples were drawn at periodic intervals and assayed using a UV-VIS spectrophotomer. Rate curves were prepared to demonstrate the amount of drug released per day, given varying percent-loadings of drug. The 30-day release profile was determined in for mitomycin-loaded stents. After a burst dose between about 25 mcg and about 60 mcg the first day, the mitomycin eluting stent delivered up to 30 days in a smooth-shaped kinetic release curves shown in FIG. 33.

As shown in FIG. 33, the various burst dosages resulted in varying kinetic release curves. Coronary angiogram and intravascular ultrasound (IVUS) imaging assessment of the treated arterial segments was performed following the same procedure as at the baseline and post-implantation. Coronary artery blood flow was assessed and a TIMI (thrombolysis in myocardial infarction) score assigned. By angiography, there was no evidence of in-stent restenosis in the stents implanted in the suitable vessel segments in each coronary artery. The restenosis rate was 0% and then flow was TIMI III. There was evidence of mild to moderate restenosis (<50%) at both ends in both stents ("edge effect") visible at angiography. By IVUS, there was total abolition of neointimal formation in the entire stent length in the stents. The edge effect was evident in the stents also by IVUS.

The present invention is a method of inhibiting the growth of smooth muscle cells to inhibit restenosis comprising: providing a biocompatible implantable medical device; preparing a biocompatible polymer matrix; co-solubilizing the biocompatible polymer matrix with a drug in a solvent to form a biocompatible drug release matrix; applying the biocompatible drug release matrix to the biocompatible implantable medical device to form an elution layer of the biocompatible drug release matrix on the biocompatible implantable medical device; allowing the solvent to evaporate; and implanting the biocompatible implantable medical device into a vasculature of a body.

The present invention is a method of inhibiting the proliferation of smooth muscle cells after a stent implantation comprising: providing a stent; preparing a biocompatible polymer matrix; co-solubilizing the biocompatible polymer matrix with a drug in a solvent to form a solution; applying the solution onto the stent to form an elution layer of a biocompatible drug release matrix on the biocompatible implantable medical device; allowing the solvent to evaporate; engaging the stent onto a balloon of a balloon catheter; delivering the balloon catheter with the stent engaged onto the balloon of the balloon catheter into a vasculature of a body to a treatment site; and inflating the balloon of the balloon catheter to increase a diameter of the stent to implant the stent.

The present invention is a method of inhibiting restenosis comprising: providing a medical device; applying a biocompatible drug eluting matrix comprising a biocompatible polymer matrix incorporating an analogue related to the quinone-containing alkylating agents of a mitomycin family to the medical device; and implanting the biocompatible implantable medical device into a vessel to elute the analogue related to the quinone-containing alkylating agents of a mitomycin family.

The present invention is an apparatus and a method for delivery of mitomycin through an eluting biocompatible implantable medical device. Mitomycin C causes inhibition of smooth muscle cell proliferation in an anaerobic (low oxygen) environment. The present invention provides an effective method of treating a localized area of a diseased vasculature after delivery of a biocompatible implantable medical device that provides a coating that elutes mitomycin C at a controlled rate that inhibits the proliferation of smooth muscle cells causing restenosis, is reliable in consistently treating the localized area over a period of time and does not adversely affect healthy tissue proximal to an area of treatment.

All patents, patent applications, and published references cited herein are hereby incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A biocompatible drug release matrix for a medical device comprising:
   a biocompatible polymer matrix comprising a thermoplastic polyurethane elastomer; and
   a drug incorporated into the biocompatible polymer matrix,
wherein the biocompatible polymer matrix is co-solubilized with the drug in a solvent to form a solution wherein the drug forms a plurality of small particles in the solution and the solvent is evaporated from the solution.

2. The biocompatible drug release matrix of claim 1 wherein the drug has antibiotic properties and anti-proliferative properties.

3. The biocompatible drug release matrix of claim 1 wherein the drug is an analogue related to the quinone-containing alkylating agents of a mitomycin family.

4. The biocompatible drug release matrix of claim 1 wherein the drug is mitomycin C.

5. The biocompatible drug release matrix of claim 1 wherein a ratio of the weight of the biocompatible polymer matrix and the drug is about 4 to about 1.

6. The biocompatible drug release matrix of claim 1 wherein the solvent is selected from the group consisting of water, saline, tetrahydrofuran, methanol, acetone, butyl acetate, cyclohexane, carbon tetrachloride, ether, chloroform, benzene, ethanol, toluene, dimethyl sulfoxide, petroleum ethers, other hydrocarbons and other organic solvents.

7. The biocompatible drug release matrix of claim 1 wherein the biocompatible polymer matrix further comprises polyvinyl pyrrolidone with an at least one isocyanate.

8. The biocompatible drug release matrix of claim 1 wherein the biocompatible polymer matrix further comprises a mixture of hydrophilic and hydrophobic polymers selected from the group consisting of polyurethanes, polyvinyl pyrrolidone, poly methyl methracrylate (PMMA), hydroxyetyl methacrylate and cellulose esters.

9. The biocompatible drug release matrix of claim 1 wherein the biocompatible polymer matrix further comprises an erodible polymer.

10. The biocompatible drug release matrix of claim 9 wherein the erodible polymer is selected from the group consisting of polyactide, polyactide with glycolide, polyester-amides, polyurethanes, poly(ethylene-urethane), poly(ester-urethane) and poly(ether-polyester-urethane), amino-acid based polyurethanes, polycaprolactone based polyurethanes, polyurethanes synthesized from poly(butylene succinate) polyol, poly(ethylene glycol), and 4,4'-methylenebis(cyclohexyl isocyanate), fat, carbohydrates and protein compounds.

11. The biocompatible drug release matrix of claim 1 wherein the biocompatible polymer matrix further comprises parylene and derivatives of parylene.

12. The biocompatible drug release matrix of claim 1 wherein the biocompatible polymer matrix further comprises polybutylmethacrylate and polyethylenevinylacetate.

13. The biocompatible drug release matrix of claim 12 wherein the concentrations of polybutylmethacrylate and polyethylenevinylacetate are approximately equal.

14. The biocompatible drug release matrix of claim 1 wherein the biocompatible polymer matrix further comprises a polymer selected from the group consisting of hybrid polymers, composites and polymer blends, acrylate terpolymers, tri-block polymers, polyethylene vinyl-acetate methacrylic tri-block terpolymer, ethyl-vinyl acetate, polyethyl vinyl-acetate, polybutyl methacrylic acid and polyethyl vinyl-acetate blends, polyurethanes and polyurethane-polycarbonate blends, silicone-urethane copolymers, polyvinyl pyrrolidone, polyester resins and parylene.

15. A biocompatible drug release matrix for a medical device comprising:
a biocompatible drug eluting matrix comprising polybutylmethacrylate and polvethylenevinylacetate; and
a drug incorporated into the biocompatible drug eluting matrix,
wherein the drug is an analogue related to the quinone-containing alkylating agents of a mitomycin family and wherein the drug forms a plurality of small particles in a solution.

16. The biocompatible drug release matrix of claim 15 wherein the drug is mitomycin C.

17. The biocompatible drug release matrix of claim 15 wherein the biocompatible drug eluting matrix releases the drug at a rate sufficient to maintain tissue level concentrations of the drug from about 0.01 micrograms per milliliter to about 25 micrograms per milliliter of the surrounding tissue for at least two weeks after implantation of the medical device.

18. The biocompatible drug release matrix of claim 15 wherein the biocompatible drug eluting matrix has a concentration of the drug between about 0.1 micrograms and about 101 micrograms per millimeter of medical device length.

19. The biocompatible drug release matrix of claim 15 wherein the biocompatible drug eluting matrix has a concentration of the drug between about 0.02 µg/mm$^2$ and about 2.5 µg/mm$^2$ per medical device surface area.

20. The biocompatible drug release matrix of claim 15 wherein the medical device is coated with a total dosage of about 10 micrograms of the drug per millimeter length of the medical device.

21. The biocompatible drug release matrix of claim 15 wherein the medical device is coated with a total dosage of about 0.5 micrograms to about 50 micrograms of the drug per millimeter length of the medical device.

22. The biocompatible drug release matrix of claim 15 wherein an initial dose of between about 10 percent to about 60 percent of the drug is delivered to the tissue in the first few days after implantation of the medical device.

23. The biocompatible drug release matrix of claim 15 wherein at least a portion of a remainder of the drug is delivered at a slower rate than an initial dose of the drug.

24. The biocompatible drug release matrix of claim 15 further comprising a burst control layer to reduce the rate of diffusion of the drug from the biocompatible drug release matrix.

25. The biocompatible drug release matrix of claim 15 wherein mitomycin C is eluted from the biocompatible drug release matrix at a controlled rate.

26. The biocompatible drug release matrix of claim 15 wherein the biocompatible drug release matrix is incorporated within a vascular prosthesis.

27. The biocompatible drug release matrix of claim 15 wherein the biocompatible drug release matrix comprises a coating applied to the surface of a vascular prosthesis.

28. The biocompatible drug release matrix of claim 15 wherein the biocompatible drug release matrix comprises a film which covers a vascular prosthesis.

29. The biocompatible drug release matrix of claim 15 wherein the biocompatible drug release matrix is co-solubilized with the drug in a solvent to form a solution and the solvent is evaporated from the solution.

30. The biocompatible drug release matrix of claim 15 further comprising polyvinyl pyrrolidone with an at least one isocyanate.

31. The biocompatible drug release matrix of claim 15 further comprising an erodible polymer.

32. The biocompatible drug release matrix of claim 15 wherein the erodible polymer is selected from the group consisting of polyactide, polyactide with glycolide, polyester-amides, polyurethanes, poly(ethylene-urethane), poly(ester-urethane) and poly(ether-polyester-urethane), amino-acid based polyurethanes, polycaprolactone based polyurethanes, polyurethanes synthesized from poly(butylene succinate) polyol, poly(ethylene glycol), and 4,4'-methylenebis(cyclohexyl isocyanate), fat, carbohydrates and protein compounds.

33. The biocompatible drug release matrix of claim 1 wherein the drug is linked to a compound to alter the release kinetics, decrease the toxicity or enhance the potency of the drug.

34. The biocompatible drug release matrix of claim 1 wherein the biocompatible polymer matrix comprises a plurality of sub-layers.

35. The biocompatible drug release matrix of claim 34 wherein the plurality of sub-layers have varying chemical compositions.

36. The biocompatible drug release matrix of claim 34 wherein an amount of the drug incorporated into the biocompatible polymer matrix varies from one sub-layer to an adjacent sub-layer.

37. The biocompatible drug release matrix of claim 34 wherein an amount of drug incorporated into the biocompatible polymer matrix is approximately the same from one sub-layer to an adjacent sub-layer.

38. The biocompatible drug release matrix of claim 34 wherein the plurality of sub-layers have the same chemical composition.

39. The biocompatible drug release matrix of claim 1 wherein the biocompatible polymer matrix comprises a single layer.

40. A biocompatible drug release matrix comprising:
   a biocompatible drug eluting matrix comprising a thermoplastic polyurethane elastomer; and
   a drug incorporated into the biocompatible drug eluting matrix,
wherein the biocompatible drug eluting matrix is co-solubilized with the drug in a solvent to form a solution wherein the drug forms a plurality of small particles in the solution and the solvent is evaporated from the solution.

41. The biocompatible drug release matrix of claim 40 wherein the biocompatible drug eluting matrix comprises a plurality of sub-layers.

42. The biocompatible drug release matrix of claim 41 wherein an amount of drug incorporated into the biocompatible drug eluting matrix varies from one sub-layer to an adjacent sub-layer.

43. The biocompatible drug release matrix of claim 41 wherein an amount of drug incorporated into the biocompatible drug eluting matrix is approximately the same from one sub-layer to an adjacent sub-layer.

44. The biocompatible drug release matrix of claim 40 wherein the biocompatible drug eluting matrix comprises a single layer.

45. The biocompatible drug release matrix of claim 40 wherein the drug is linked to a compound to alter the release kinetics, decrease the toxicity or enhance the potency of the drug.

46. The biocompatible drug release matrix of claim 40 wherein the biocompatible drug release matrix is applied to a stent.

47. The biocompatible drug release matrix of claim 40 wherein the biocompatible drug release matrix is applied to a medical device.

48. The biocompatible drug release matrix of claim 47 wherein the biocompatible drug eluting matrix releases the drug at a rate sufficient to maintain tissue level concentrations of the drug from about 0.01 micrograms per milliliter to about 25 micrograms per milliliter of the surrounding tissue for at least two weeks after implantation of the medical device.

49. The biocompatible drug release matrix of claim 47 wherein the biocompatible drug eluting matrix has a concentration of the drug between about 0.1 micrograms and about 101 micrograms per millimeter of medical device length.

50. The biocompatible drug release matrix of claim 47 wherein the biocompatible drug eluting matrix has a concentration of the drug between about 0.02 $\mu g/mm^2$ and about 2.5 $\mu g/mm^2$ per medical device surface area.

51. The biocompatible drug release matrix of claim 47 wherein an initial dose of between about 10 percent to about 60 percent of the drug is delivered to the tissue in the first few days after implantation of the medical device.

52. The biocompatible drug release matrix of claim 40 wherein the drug has antibiotic properties and anti-proliferative properties.

53. The biocompatible drug release matrix of claim 40 wherein the drug is an analogue related to the quinone-containing alkylating agents of a mitomycin family.

54. The biocompatible drug release matrix of claim 40 wherein a ratio of the weight of the biocompatible drug eluting matrix and the drug is about 4 to about 1.

55. The biocompatible drug release matrix of claim 40 wherein the biocompatible drug eluting matrix further comprises polyvinyl pyrrolidone with an at least one isocyanate.

56. The biocompatible drug release matrix of claim 40 wherein the biocompatible drug eluting matrix further comprises a mixture of hydrophilic and hydrophobic polymers selected from the group consisting of polyurethanes, polyvinyl pyrrolidone, poly methyl methracrylate (PMMA), hydroxyetyl methacrylate and cellulose esters.

57. The biocompatible drug release matrix of claim 40 wherein the biocompatible drug eluting matrix further comprises an erodible polymer.

58. The biocompatible drug release matrix of claim 56 wherein the drug is entrapped into the mixture of hydrophilic and hydrophobic polymers of the biocompatible drug eluting matrix.

59. The biocompatible drug release matrix of claim 40 further comprising a metallic surface.

60. The biocompatible drug release matrix of claim 40 wherein the biocompatible drug eluting matrix further comprises polybutylmethacrylate and polyethylenevinylacetate.

61. The biocompatible drug release matrix of claim 40 wherein the drug remains part of the biocompatible drug eluting matrix.

62. The biocompatible drug release matrix of claim 40 wherein the biocompatible drug eluting matrix further comprises a polymer selected from the group consisting of hybrid polymers, composites and polymer blends, acrylate terpolymers, tri-block polymers, polyethylene vinyl-acetate methacrylic tri-block terpolymer, ethyl-vinyl acetate, polyethyl vinyl-acetate, polybutyl methacrylic acid and polyethyl vinyl-acetate blends, polyurethanes and polyurethane-polycarbonate blends, silicone-urethane copolymers, polyvinyl pyrrolidone, polyester resins and parylene.

63. A biocompatible drug release matrix comprising:
   a biocompatible polymer matrix comprising polybutylmethacrylate and polvethylenevinylacetate; and
   a drug suspended within the biocompatible polymer matrix,
wherein the drug is an analogue related to the quinone-containing alkylating agents of a mitomycin family and wherein the drug forms a plurality of small particles in a solution.

64. The biocompatible drug release matrix of claim 63 wherein the drug is mitomycin C.

65. The biocompatible drug release matrix of claim 63 wherein the biocompatible polymer matrix comprises a plurality of sub-layers.

66. The biocompatible drug release matrix of claim 65 wherein an amount of drug suspended within the biocompatible polymer matrix varies from one sub-layer to an adjacent sub-layer.

67. The biocompatible drug release matrix of claim 65 wherein an amount of drug suspended within the biocompatible polymer matrix is approximately the same from one sub-layer to an adjacent sub-layer.

68. The biocompatible drug release matrix of claim 63 wherein the biocompatible polymer matrix comprises a single layer.

69. The biocompatible drug release matrix of claim 63 wherein the biocompatible drug release matrix is applied to a stent.

70. The biocompatible drug release matrix of claim 63 wherein the biocompatible drug release matrix is applied to a medical device.

71. The biocompatible drug release matrix of claim 70 wherein the biocompatible polymer matrix releases the drug at a rate sufficient to maintain tissue level concentrations of the drug from about 0.01 micrograms per milliliter to about 25 micrograms per milliliter of the surrounding tissue for at least two weeks after implantation of the medical device.

72. The biocompatible drug release matrix of claim 70 wherein the biocompatible polymer matrix has a concentration of the drug between about 0.1 micrograms and about 101 micrograms per millimeter of medical device length.

73. The biocompatible drug release matrix of claim 70 wherein the biocompatible polymer matrix has a concentration of the drug between about 0.02 $\mu g/mm^2$ and about 2.5 $\mu g/mm^2$ per medical device surface area.

74. The biocompatible drug release matrix of claim 70 wherein an initial dose of between about 10 percent to about 60 percent of the drug is delivered to the tissue in the first few days after implantation of the medical device.

75. The biocompatible drug release matrix of claim 63 wherein the drug is linked to a compound to alter the release kinetics, decrease the toxicity or enhance the potency of the drug.

76. The biocompatible drug release matrix of claim 63 wherein the drug remains part of the biocompatible polymer matrix.

77. The biocompatible drug release matrix of claim 63 wherein the drug has antibiotic properties and anti-proliferative properties.

78. The biocompatible drug release matrix of claim 63 wherein a ratio of the weight of the biocompatible polymer matrix and the drug is about 4 to about 1.

79. The biocompatible drug release matrix of claim 63 wherein the solvent is selected from the group consisting of water, saline, tetrahydrofuran, methanol, acetone, butyl acetate, cyclohexane, carbon tetrachloride, ether, chloroform, benzene, ethanol, toluene, dimethyl sulfoxide, petroleum ethers, other hydrocarbons and other organic solvents.

80. The biocompatible drug release matrix of claim 63 further comprising a metallic surface.

81. The biocompatible drug release matrix of claim 63 wherein the biocompatible polymer matrix further comprises a mixture of hydrophilic and hydrophobic polymers selected from the group consisting of polyurethanes, polyvinyl pyrrolidone, poly methyl methracrylate (PMMA), hydroxyetyl methacrylate and cellulose esters.

82. The biocompatible drug release matrix of claim 63 wherein the biocompatible polymer matrix further comprises an erodible polymer.

83. The biocompatible drug release matrix of claim 63 wherein the biocompatible polymer matrix further comprises parylene and derivatives of parylene.

84. The biocompatible drug release matrix of claim 63 wherein the biocompatible polymer matrix further comprises a thermoplastic polyurethane elastomer.

85. The biocompatible drug release matrix of claim 63 wherein the biocompatible polymer matrix further comprises a polymer selected from the group consisting of hybrid polymers, composites and polymer blends, acrylate terpolymers, tri-block polymers, polyethylene vinyl-acetate methacrylic tri-block terpolymer, ethyl-vinyl acetate, polyethyl vinyl-acetate, polybutyl methacrylic acid and polyethyl vinyl-acetate blends, polyurethanes and polyurethane-polycarbonate blends, silicone-urethane copolymers, polyvinyl pyrrolidone, polyester resins and parylene.

86. A biocompatible drug release matrix for a medical device comprising:
a biocompatible drug eluting matrix comprising parylene and derivatives of parylene; and
a drug incorporated into the biocompatible drug eluting matrix,
wherein the biocompatible drug eluting matrix is co-solubilized with the drug in a solvent to form a solution wherein the drug forms a plurality of small particles in the solution and the solvent is evaporated from the solution to form a uniform distribution of drug in the biocompatible drug eluting matrix.

87. The biocompatible drug release matrix of claim 86 wherein the biocompatible drug eluting matrix comprises a plurality of sub-layers.

88. The biocompatible drug release matrix of claim 86 wherein the biocompatible drug eluting matrix comprises a single layer.

89. The biocompatible drug release matrix of claim 86 wherein the drug is linked to a compound to alter the release kinetics, decrease the toxicity or enhance the potency of the drug.

90. The biocompatible drug release matrix of claim 86 wherein the drug has antibiotic properties and anti-proliferative properties.

91. The biocompatible drug release matrix of claim 86 wherein the drug is an analogue related to the quinone-containing alkylating agents of a mitomycin family.

92. The biocompatible drug release matrix of claim 86 wherein the biocompatible drug eluting matrix releases the drug at a rate sufficient to maintain tissue level concentrations of the drug from about 0.01 micrograms per milliliter to about 25 micrograms per milliliter of the surrounding tissue for at least two weeks after implantation of the medical device.

93. The biocompatible drug release matrix of claim 86 wherein the biocompatible drug eluting matrix has a concentration of the drug between about 0.1 micrograms and about 101 micrograms per millimeter of medical device length.

94. The biocompatible drug release matrix of claim 86 wherein the biocompatible drug eluting matrix has a concentration of the drug between about 0.02 $\mu g/mm^2$ and about 2.5 $\mu g/mm^2$ per medical device surface area.

95. The biocompatible drug release matrix of claim 86 wherein an initial dose of between about 10 percent to about 60 percent of the drug is delivered to the tissue in the first few days after implantation of the medical device.

96. A biocompatible drug release matrix for a medical device comprising:
a biocompatible polymer matrix comprising parylene and derivatives of parylene; and
a drug suspended within the biocompatible polymer matrix, wherein the biocompatible polymer matrix is co-solubilized with the drug in a solvent to form a solution wherein the drug forms a plurality of small particles in the solution and the solvent is evaporated from the solution to form a uniform distribution of drug in the biocompatible polymer matrix.

97. The biocompatible drug release matrix of claim 96 wherein the drug is an analogue related to the quinone-containing alkylating agents of a mitomycin family.

98. The biocompatible drug release matrix of claim 96 wherein the biocompatible polymer matrix releases the drug at a rate sufficient to maintain tissue level concentrations of the drug from about 0.01 micrograms per milliliter to about 25 micrograms per milliliter of the surrounding tissue for at least two weeks after implantation of the medical device.

99. The biocompatible drug release matrix of claim 96 wherein the biocompatible polymer matrix has a concentration of the drug between about 0.1 micrograms and about 101 micrograms per millimeter of medical device length.

* * * * *